US008365601B2

(12) United States Patent
Minachi et al.

(10) Patent No.: US 8,365,601 B2
(45) Date of Patent: Feb. 5, 2013

(54) HIGH PRECISION CORROSION MONITORING SENSOR ASSEMBLY AND SYSTEM

(75) Inventors: Ali Minachi, Dhahran (SA); Ghazzay M. Al-Subaii, Eastern Province (SA); Ayedh S. Saleh, Dhahran (SA); Erika Laiche, San Antonio, TX (US); Glenn Light, San Antonio, TX (US)

(73) Assignee: Saudi Arabian Oil Company (SA)

( * ) Notice: Subject to any disclaimer, the term of this patent is extended or adjusted under 35 U.S.C. 154(b) by 214 days.

(21) Appl. No.: 12/983,931

(22) Filed: Jan. 4, 2011

(65) Prior Publication Data
US 2012/0167688 A1 Jul. 5, 2012

(51) Int. Cl.
*G01N 29/04* (2006.01)
(52) U.S. Cl. ............................ 73/602; 73/644
(58) Field of Classification Search ............ 73/602, 73/644, 861.27
See application file for complete search history.

(56) References Cited

U.S. PATENT DOCUMENTS

| | | | |
|---|---|---|---|
| 3,934,457 A | 1/1976 | Clark et al. | |
| 3,989,213 A * | 11/1976 | Allen | 248/214 |
| 4,242,744 A | 12/1980 | Rottmar | |
| 4,398,424 A | 8/1983 | Abts | |
| 5,463,905 A * | 11/1995 | Baird | 73/861.25 |
| 5,549,000 A | 8/1996 | Brown | |
| 5,619,423 A | 4/1997 | Scrantz | |
| 6,463,813 B1 | 10/2002 | Gysling | |
| 6,513,385 B1 | 2/2003 | Han | |
| 6,578,422 B2 | 6/2003 | Lam | |
| 6,578,424 B1 | 6/2003 | Ziola | |
| 7,100,462 B2 | 9/2006 | Gronvall | |
| 7,201,055 B1 | 4/2007 | Bagley | |
| 7,624,651 B2 * | 12/2009 | Fernald et al. | 73/861.27 |
| 7,669,483 B1 | 3/2010 | Felleer | |
| 7,680,625 B2 | 3/2010 | Trowbridge | |
| 7,900,346 B2 | 3/2011 | Fogarty et al. | |

(Continued)

FOREIGN PATENT DOCUMENTS

DE 102007043364 4/2009
EP 753729 * 1/1997

(Continued)

OTHER PUBLICATIONS

PCT International Search Report, Apr. 10, 2012.

(Continued)

*Primary Examiner* — J M Saint Surin
(74) *Attorney, Agent, or Firm* — Bracewell & Giuliani LLP

(57) ABSTRACT

A high-precision corrosion monitoring sensor assembly is provided for permanent mounting on a vessel to measure wall thickness of the vessel. The assembly includes an ultrasonic transducer and a delay line, which are bonded to the vessel wall a first location. The assembly is further bonded to the vessel by an adjustable fixture. The assembly includes a cross-member attached to the ultrasonic transducer, having a pivot pin at each distal end. The pivot pins are attached to a first tower and a second tower, which bond to the outer vessel wall at a second location and a third location. The position of the first and second towers can be adjusted with respect to angle and placement about the pivot pins. Fasteners are attached to the pivot pins and can be tightened to make rigid the fixture, thereby allowing configuration of the assembly for use on flat surfaces and small-diameter pipes.

22 Claims, 14 Drawing Sheets

U.S. PATENT DOCUMENTS

| | | | |
|---|---|---|---|
| 7,950,298 B2 * | 5/2011 | Lavoie et al. | 73/866.5 |
| 7,963,175 B2 * | 6/2011 | Gysling | 73/861.27 |
| 7,975,549 B2 | 7/2011 | Fetzer et al. | |
| 7,997,139 B2 * | 8/2011 | Owens et al. | 73/622 |
| 2007/0193357 A1 | 8/2007 | Daaland et al. | |
| 2008/0307637 A1 | 12/2008 | Fogarty et al. | |
| 2008/0314154 A1 | 12/2008 | Fetzer et al. | |
| 2010/0236330 A1 | 9/2010 | Nyholt et al. | |

FOREIGN PATENT DOCUMENTS

| | | | |
|---|---|---|---|
| EP | 0952446 | | 10/1999 |
| EP | 2053391 | | 4/2009 |
| JP | 10048173 | * | 2/1998 |

OTHER PUBLICATIONS

Graham, Benny, et al, "A Wireless Sensor Network of Permanently Installed Structural Integrity Monitors," AIP Conference Proceedings, Jul. 30, 2004, pp. 1757-1764, vol. 760, University of Strathclyde, Glasgow, Scotland, UK.

* cited by examiner

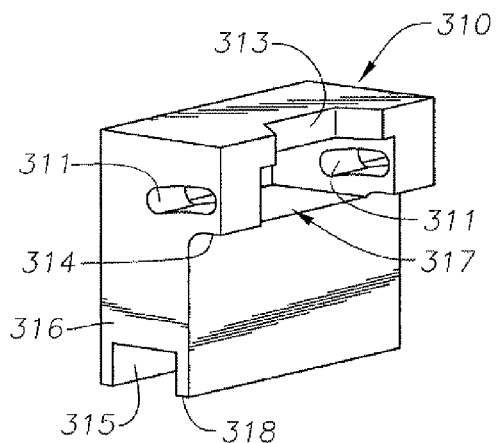
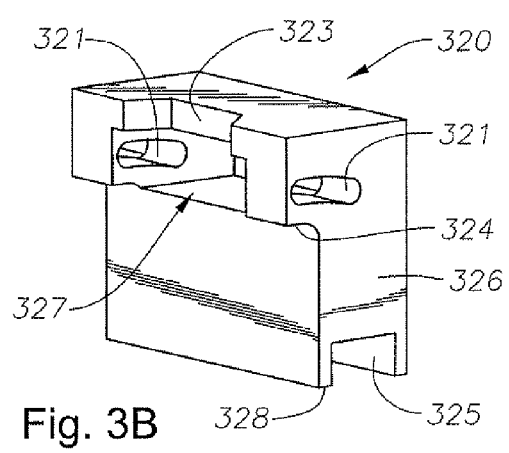
Fig. 3A    Fig. 3B
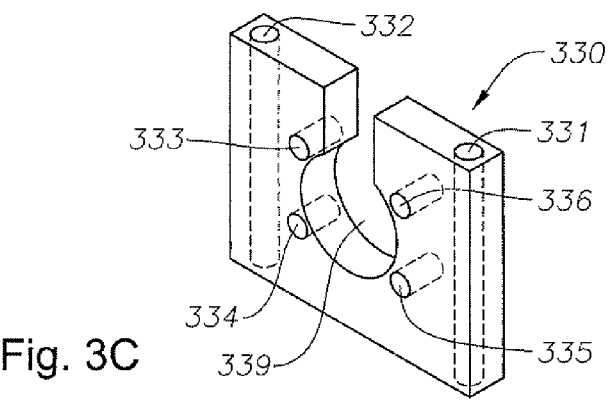
Fig. 3C
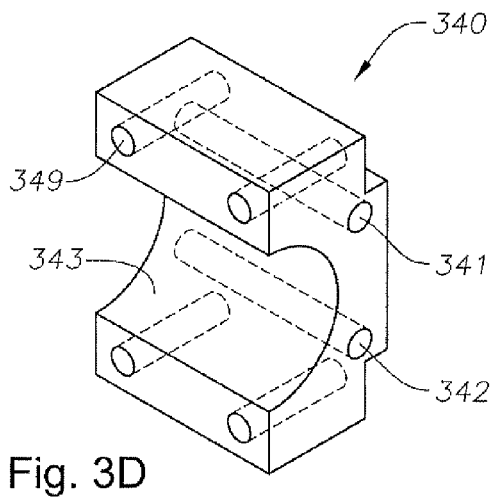
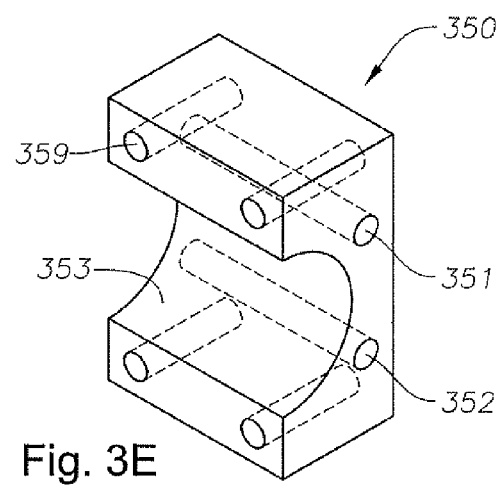
Fig. 3D    Fig. 3E 10 MHz Nominal Delay Line
Transducer Frequency Response

HIGH PRECISION CORROSION MONITORING SENSOR ASSEMBLY AND SYSTEM

BACKGROUND OF THE INVENTION

1. Area of the Invention

The invention relates generally to the field of petrochemical pipelines and, in particular, to the field of electronic detection and monitoring of corrosion in petrochemical pipelines.

2. Description of the Related Art

Pipelines in petrochemical industries are often susceptible to damage caused by excessive corrosion. The life expectancy of a pipe before failure mostly depends on the chemical and physical properties of transported gaseous or liquid media, the environmental condition surrounding the pipe and a suitable cathodic protection (CP) system which prevents anodic behavior leading to metal loss. In some cases, only certain locations of pipes are exposed to considerable corrosion. If such corrosion in pipes is not detected and monitored, it can lead to damage, failure, and spills, which can result in undesirable consequences including monetary loss, safety hazards, and environmental damage. Accordingly, regular on-stream inspection (OSI) of pipes is an essential risk management procedure.

Corrosion, such as pitting in the interior walls of ferrous pipeline, is likely to occur at isolated so-called "critical" areas or locations of the pipe. At times, critical locations are difficult to reach for the purpose of OSI. Scaffolding or excavation operations, for example, are usually required to access the critical areas of the pipe. To perform such operations on a regular basis is often impractical and expensive and requires large-scale movement of equipment and personnel.

Solutions for remote monitoring of critical areas of pipeline is known in the art, for example, using electronic monitors on the outer surface of a pipe. However, such solutions exhibit one or more disadvantages, including: (i) lacking the structural rigidity to allow targeting isolated locations on a pipeline to obtain consistent measurement with high precision, (ii) being unable to accommodate larger and more accurate ultrasonic transducers or the addition of a delay line, (iii) being unable to withstand environmental factors such as high temperature pipeline surfaces, erosion by wind or sand, or corrosion of the transducer or clamp equipment, and (iv) lacking the adjustability to readily accommodate for mounting on divergent pipe sizes or flat surfaces.

Accordingly, there is a need in the art for a high-precision corrosion monitoring assembly capable of mounting highly accurate electronic monitoring equipment on remote pipe locations and having the structural rigidity sufficient to obtain consistent measurements at precise locations on a pipeline. There is also a need in the art for a high-precision corrosion monitoring assembly having a structure and material properties to withstand environmental factors for permanent installation. There is also a need in the art for such an assembly capable of providing such rigidity, such structure, and such material properties while also accommodating larger, more accurate transducers and a delay line. There is also a need in the art for a high-precision corrosion monitoring assembly having both rigidity and adjustability allowing the assembly to be readily deployed on any of divergent pipe sizes or flat surfaces that can be found in a facility.

SUMMARY OF THE INVENTION

Applicants recognize the disadvantages of the related art, and in the present invention, have provided embodiments that advantageously allow larger, more accurate transducers, including transducers having delay lines attached thereto, to be permanently mounted on remote, inaccessible pipe locations.

Embodiments of the present invention provide an enhanced clamping fixture referred to as a transducer hold-down fixture (THDF) allowing the permanent installation of a highly accurate 5-MHz-10-MHz transducer having a delay line (approximately 15 mm in additional stack height) attached thereto to improve the accuracy of the readings at the transducer. The lateral forces acting upon the transducer due to environmental factors in the field, in particular with respect to the height of the transducer and the attached delay line, are likely to compromise or de-bond an epoxy bond between the transducer (or delay line) and the pipe without additional support. Embodiments of the present invention provide a THDF having two additional bonding points on the pipe and a structure having sufficient rigidity to maintain the mounting location of the transducer with a high degree of precision.

Embodiments of the present invention provide a rigid structure that not only accommodates the shape of such highly accurate transducers and attached delay lines, but also is adjustable to accommodate installation on pipes having any diameter selected from a range of diameters. For example, embodiments of the present invention provide a rigid THDF that mounts to a pipe having an outer diameter greater than or equal to six (6) inches, including a flat surface ("the diameter range"). With reference to FIG. 4, the critical dimensions can be shown for providing a THDF having the level of adjustability for accommodating the transducers described herein, including a delay line, throughout the diameter range. Embodiments of the present invention are adjustable so that, regardless of the diameter of the pipe on which it is installed, the rigidity of the THDF and the forces applied by the THDF to the pipe are constant throughout the diameter range. Because embodiments of the present invention are both rigid and adjustable, and because the rigidity of the THDF and the forces applied thereby to the pipe are constant throughout the diameter range, the THDF allows the transducer to provide measurements with minimal error attributable to any flex or change in the configuration of the THDF due to pipe size or due to environmental factors, such as temperature.

Because embodiments of the present invention are less vulnerable to external lateral forces to de-bond the transducer, and because embodiments of the present invention allow permanent and precise positioning of the transducer at a pinpoint location, embodiments of the present invention reduce the need for personnel to routinely access the installation location for maintenance or readjustment of the assembly. Accordingly, embodiments of the present invention can be more efficiently installed at locations having inconvenient access or locations that are regularly inaccessible (such as when excavation or scaffolding is required). For example, where embodiments of the present invention are installed at 20 pipeline locations, annual savings in ongoing scaffolding and excavation costs for OSI programs can be approximately $25,000. Moreover, embodiments provide a THDF having a small footprint that minimizes the amount of excavation or scaffolding required to mount the THDF to the pipe.

Further, the accuracy and precision of measurements provided by embodiments of the present invention allow embodiments of the present invention to be employed in continuous monitoring operations where such real-time measurements can be used to ascertain corrosion rates with high fidelity, such as in controlling the injection dosage of corrosion inhibitors added to crude oil.

Embodiments of the present invention provide a high-precision corrosion monitoring sensor assembly to be permanently mounted on an outer pipe wall of a pipe for measuring remaining wall thickness of the pipe, the pipe having any diameter within a preselected range of diameters.

Embodiments of the present invention providing a high-precision corrosion monitoring sensor assembly can include an ultrasonic transducer for measuring remaining wall thickness of a pipe. In such embodiments, a first base of the ultrasonic transducer is positioned to bond to an outer pipe wall of the pipe at a first mounting location when the first base is positioned substantially tangential to the outer pipe wall at the first mounting location; and Embodiments of the present invention providing a high-precision corrosion monitoring sensor assembly include an adjustable transducer hold down fixture for housing the ultrasonic transducer and for bonding the ultrasonic transducer to the outer pipe wall at a second mounting location and at a third mounting location.

Embodiments of the present invention providing a high-precision corrosion monitoring sensor assembly with an adjustable transducer hold down fixture further include a cross-member attached to the ultrasonic transducer. A first distal end of the cross-member has a first pivot pin attached thereto, and a second distal end of the cross-member has a second pivot pin attached thereto. A first axis of rotation about the first pivot pin is substantially parallel to a second axis of rotation about the second pivot pin.

Embodiments of the present invention providing a high-precision corrosion monitoring sensor assembly with an adjustable transducer hold down fixture further include a first tower for supporting the adjustable transducer hold down fixture. A second base of the first tower is magnetic and positioned to bond to the outer pipe wall at the second mounting location when the second base is positioned substantially tangential to the outer pipe wall at the second mounting location. The first tower has a first track to receive the first pivot pin at a variable position within the first track.

Embodiments of the present invention providing a high-precision corrosion monitoring sensor assembly with an adjustable transducer hold down fixture further include a second tower for supporting the adjustable transducer hold down fixture. A third base of the second tower is magnetic and positioned to bond to the outer pipe wall at the third mounting location when the third base is positioned substantially tangential to the outer pipe wall at the third mounting location. The second tower has a second track to receive the second pivot pin at a variable position within the first track.

Embodiments of the present invention providing a high-precision corrosion monitoring sensor assembly with an adjustable transducer hold down fixture further include two or more fasteners for collectively making rigid the adjustable transducer hold down fixture by restricting adjustment of the first tower about the first pivot pin in the first track and by restricting adjustment of the second tower about the second pivot pin in the second track.

BRIEF DESCRIPTION OF THE DRAWINGS

So that the manner in which the features and advantages of the invention, as well as others which will become apparent are attained and can be understood in more detail, a more particular description of the invention briefly summarized above may be had by reference to the embodiment thereof which is illustrated in the appended drawings, which drawings form a part of this specification. It is to be noted, however, that the drawings illustrate only an embodiment of the invention and therefore are not to be considered limiting of its scope as the invention may admit to other equally effective embodiments.

FIGS. 3A-3E are schematic drawings showing oblique views of component parts of an assembly according to an embodiment of the present invention.

DETAILED DESCRIPTION OF THE INVENTION

Figure 1:
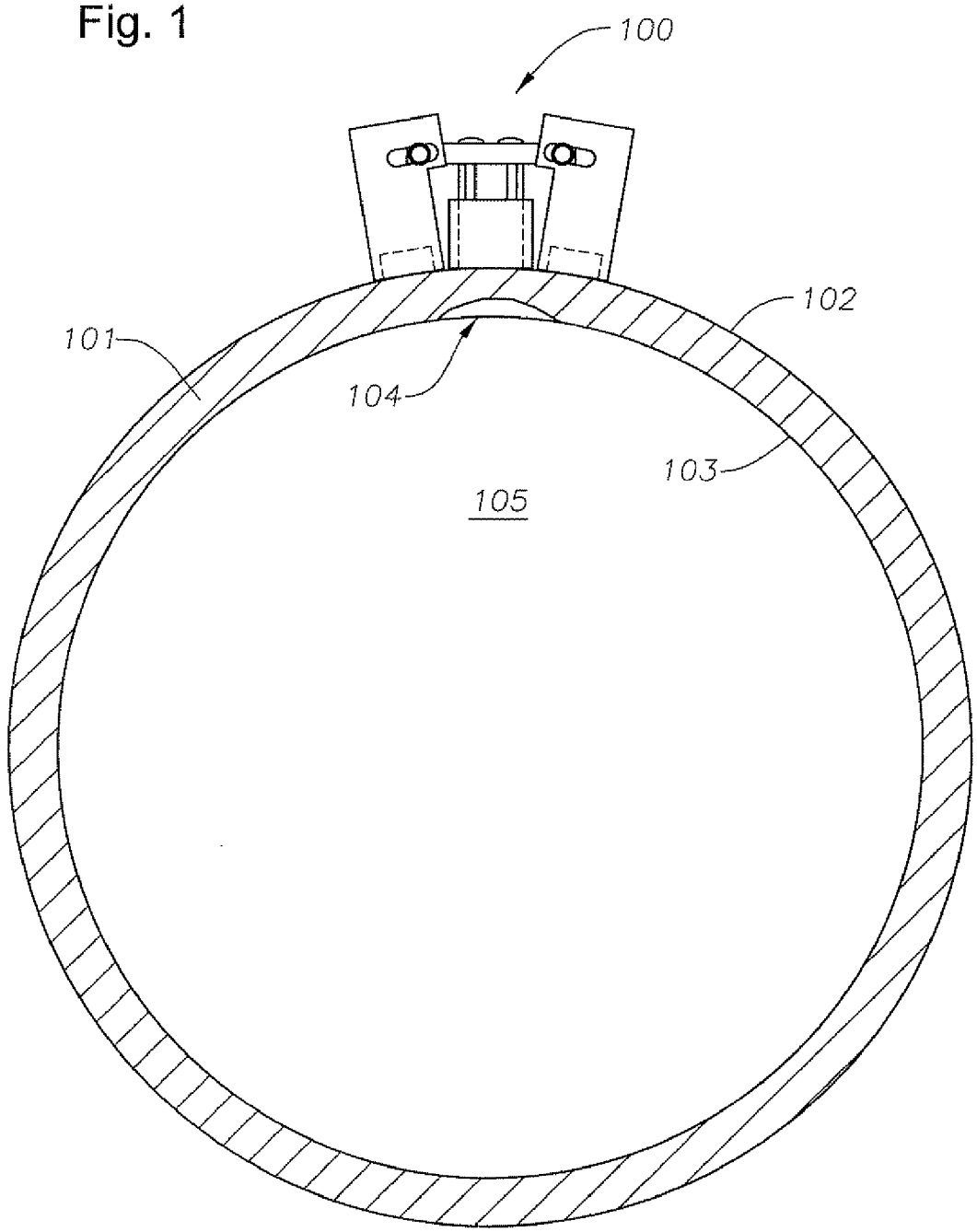
FIG. 1 is a schematic drawing showing an axial cutaway of a pipe and an assembly attached thereto according to an embodiment of the present invention.
Figure 10:
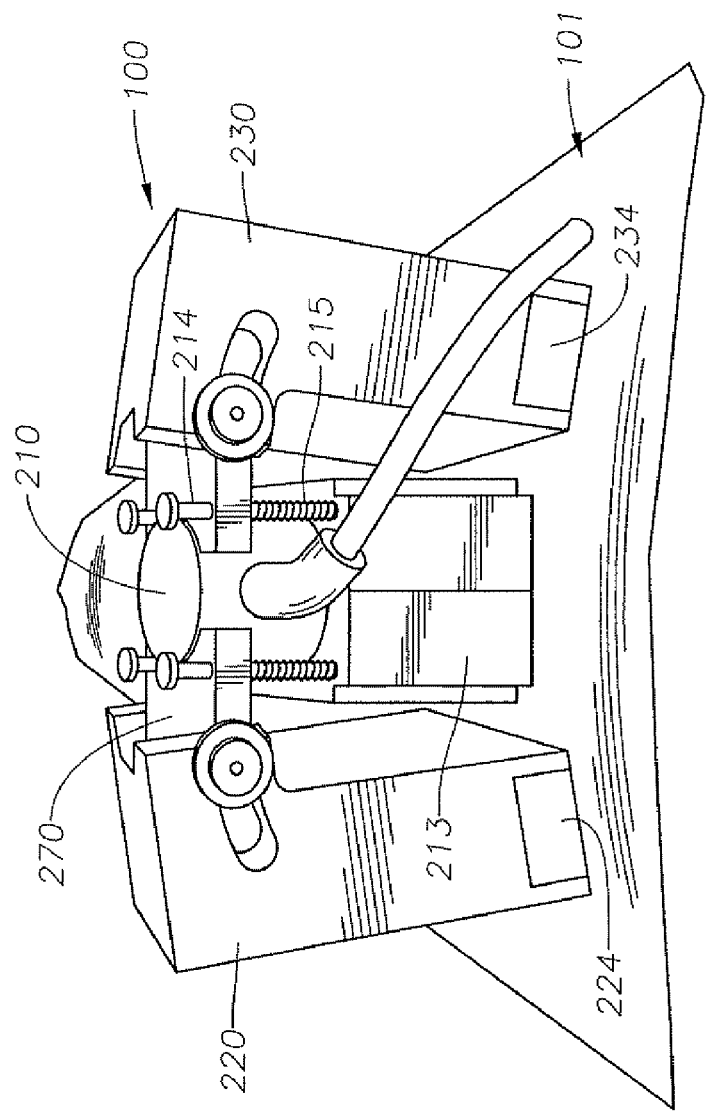
FIG. 10 is a schematic drawing showing an assembly attached to a pipe according to an embodiment of the present invention.

So that continuous wall thickness monitoring can be performed at precise location of a pipeline, a pipe, or a vessel, an embodiment of the present invention, as can be shown with reference to FIG. 1, provides a high-precision corrosion monitoring assembly 100 (HPCM) to be permanently mounted on an outer wall of the pipeline, pipe, or vessel, for example, as on outer pipe wall 102 of pipe 101. The monitoring assembly 100 may be referred to herein as the HPCM or as an "HPCM sensor" or an "HPCM assembly." With reference to FIG. 10, an HPCM 100 according to embodiments of the present invention is shown mounted to a pipe 101. Although embodiments of the present invention are described with respect to a "pipe" herein, the invention is not limited to such embodiments and can also be used with respect to other types of vessels, including those having flat surfaces.

The permanent mounting of the HPCM 100 allows for consistent measurements in multiple measurement cycles over a period of time, even where the HPCM 100 is subjected to environmental forces at the installation site. By way of example, pipe 101 is a carbon steel pipe or metal sheet having a thickness measurement in a range of 2 millimeters (mm) to 30 mm. Pipe 101 can store or transport liquid or gaseous contents, for example, that result in the outer pipe wall 102 reaching a temperature as high as 120 degrees Celsius (° C.). Pipe 101 can, for example, be fully or partially buried beneath the surface of the earth, submerged beneath the surface of the sea, or elevated in the air. Accordingly, the HPCM 100 may be subject to environmental factors including lateral forces, erosion, and corrosion caused by, for example, sand, soil, groundwater, seawater, or wind.

As can be shown with reference to FIG. 1, the HPCM 100 is positioned at a critical area of the pipeline, pipe, or vessel, such as at an area of pipe 101 where a corrosion pit 104 has previously been detected along the inner wall or surface 103 of a pipe. The location of corrosion pits can be detected, for example, using C-Scan technology, and the HPCM 100 can be installed at a position on the outer surface 102 of the pipe that corresponds to the location of the corrosion pit 104 (e.g., even at a 6-o'clock position where the HPCM 100 would be inverted). Accordingly, the HPCM 100 allows continuous and constant monitoring of the progression of corrosion pit 104 or other defects as the corrosion or defect progresses.

The HPCM 100 measures the depth of the remaining pipe thickness by implementing conventional ultrasound (UT) through compressional or longitudinal waves generated by, for example, a 10-MHz piezoelectric transducer allowing sufficient resolution and sensitivity in thickness measurements for pipes having a thickness less than or equal to 30 mm. Also, 5-MHz piezoelectric transducers can be implemented for the purpose of measuring thicker elements as needed.

Figure 2:
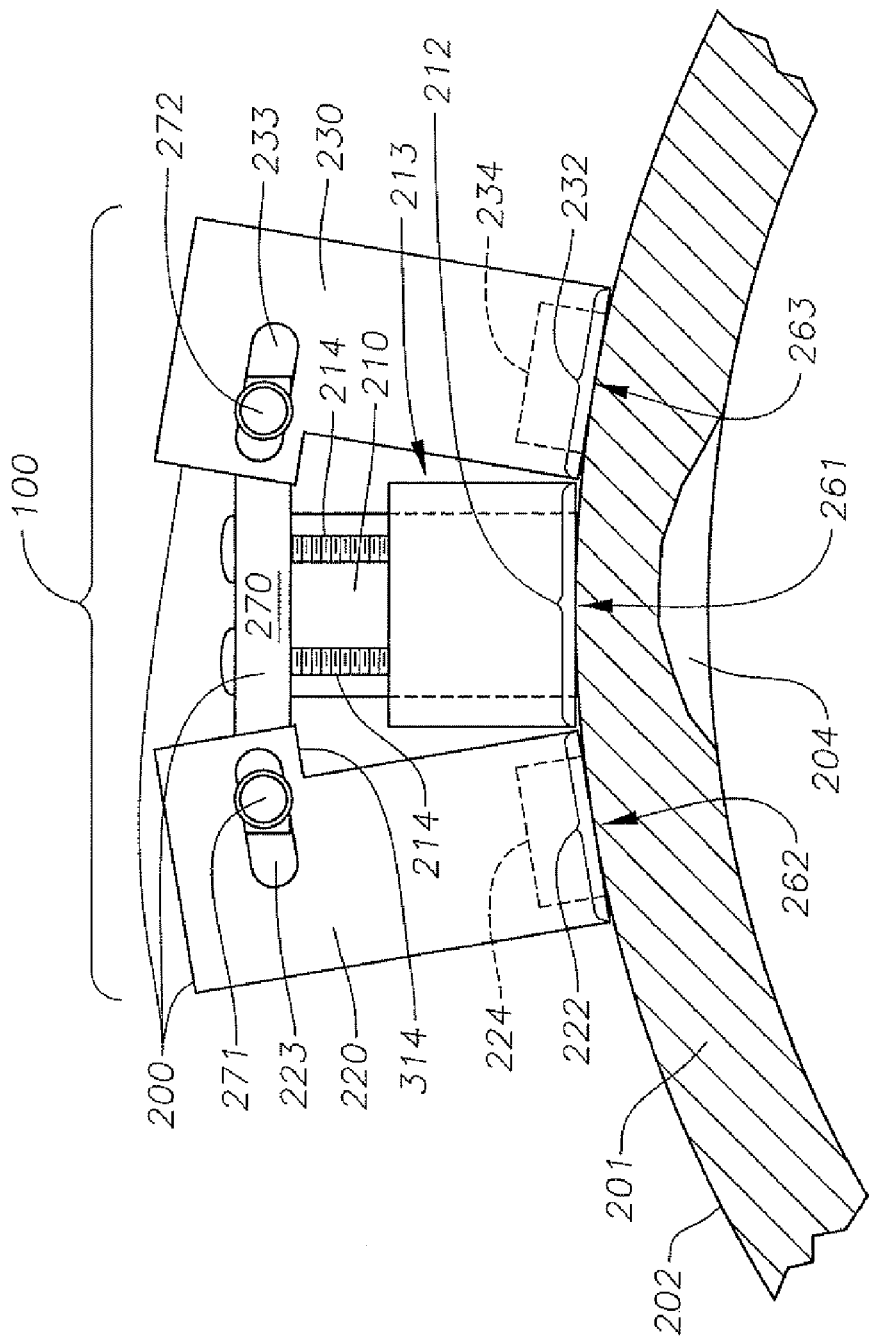
FIG. 2 is a schematic drawing showing an axial cutaway of a pipe and an assembly attached thereto according to an embodiment of the present invention.

As shown with reference to FIG. 2, the HPCM 100 includes an ultrasonic transducer 210 to measure wall thickness of a pipe 201 when the ultrasonic transducer 210 is positioned substantially normal to the outer wall 202 of the pipe 201. The ultrasonic transducer 210 can be for example, a normal-incidence single element transducer, a dual element transducer, a delay line transducer or the like. The ultrasonic transducer 210 can be selected such that it can resolve carbon steel pipe thickness measurements in the range of 2 mm to 30 mm at an accuracy of ±0.5 mm. The ultrasonic transducer 210 can also be selected such that it can operate continuously, and achieve the specified accuracy, over a temperature range including temperatures as high as 120° C.

An example of one preferred ultrasonic transducer includes a normal-incidence single-element transducer. A normal-incidence single-element transducer consists of a single encapsulated crystal oriented to transmit an ultrasonic signal normal to a contact surface, for example, at point 261 with respect to FIG. 2. The normal-incidence single-element transducer advantageously allows a simple implementation in an autonomous monitoring system. Further, a normal-incidence single-element transducer introduces the fewest number of extraneous signals into the waveform, as compared to other transducer types, which simplifies waveform analysis. Multiple reflections can be captured, allowing for a high level of confidence in thickness measurements. The normal-incidence single-element transducer, however, is the least capable to resolve minimum thickness requirements.

Ultrasonic transducer 210 can also be, for example, a dual element transducer. A dual element transducer uses a separate transmitter element and receiver element to ensure that the initial pulse of the transmitter does not affect the received waveform. Both the transmitter element and the receiver element, typically, are included in a single case. The ultrasonic signal, typically, is not directed at normal-incidence, so waveform correction is often necessary in waveform analysis. The receiver-transducer measurement is minimally affected by the transmitted signal, which advantageously allows measurements on thinner materials. Dual element transducers in the range of 2.25-MHz to 5-MHz that are capable of making pipe thickness measurements within the specified temperature range include, for example, the Olympus D790-SM, which is a 5-MHz transducer that is understood to be capable of making thickness measurements down to 1 mm. Disadvantageously, however, dual element transducers are often capable of detecting only one reliable back-wall reflection. Also, because both transmitter and receiver elements are housed in the same case, the two elements can experience cross-talk, thereby increasing acoustic and electrical noise in the measurements. Also, disadvantageously, the measurements from dual element transducers typically cannot be interpreted through time-of-flight analysis alone.

In a dual element transducer, because two elements with independent operating characteristics are used, and because the transmitted signal is typically not at normal-incidence, and because the time delays in the transmitter element and receiver element are often not equivalent, additional calibration steps are often needed to determine the true material thickness. In certain embodiments, each transducer model, and possibly each individual transducer, requires calibration prior to use. Testing of the HPCM 100 having an ultrasonic transducer 210 being an uncalibrated dual-element transducer produced results having significant error (2.5 mm-4.5 mm error) in thickness measurements. Accordingly, dual element transducers included in the autonomous monitoring sensor require each of the transducers to be calibrated prior to installation on the pipe. The calibration procedure, however, increases costs and requires greater training or responsibilities for a technician to correctly install the HPCM 100.

Figure 9:
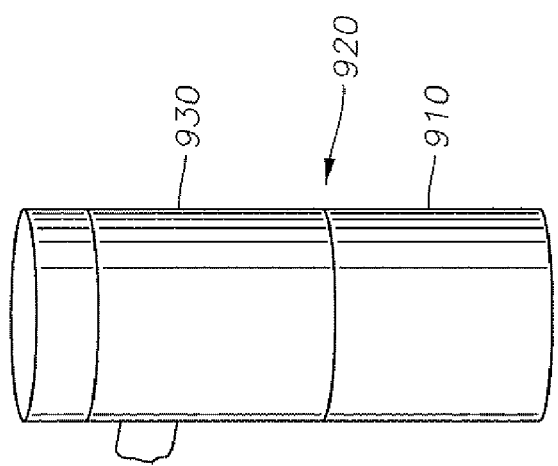
FIG. 9 is a schematic drawing showing transducer and a delay line attached thereto according to an embodiment of the present invention.

Ultrasonic transducer 210 is preferably a delay-line transducer. A delay-line transducer uses the same design as a normal-incidence single-element transducer, but the delay-line transducer includes a column of material (the "delay line") that separates the transducer front surface from the surface of the pipe. An exemplary delay line transducer is shown with reference to FIG. 9, wherein the delay line 910 is bonded to the front surface 920 of the transducer element 930.

The delay line 910 advantageously separates the front surface reflection from the initial pulse, which permits the acquisition of multiple back wall reflections in very thin walled material without interference from the initial pulse. The delay line 910 also advantageously provides thermal insulation and heat-sinking between the transducer front surface 920 and the surface of a pipe, which allows the surface temperature of the pipe to exceed the operating temperature of the transducer 930. A delay line, however, can add reflections to the waveform, which can increase the ultrasonic noise level and complicate autonomous interpretation of the waveform.

Figure 5:
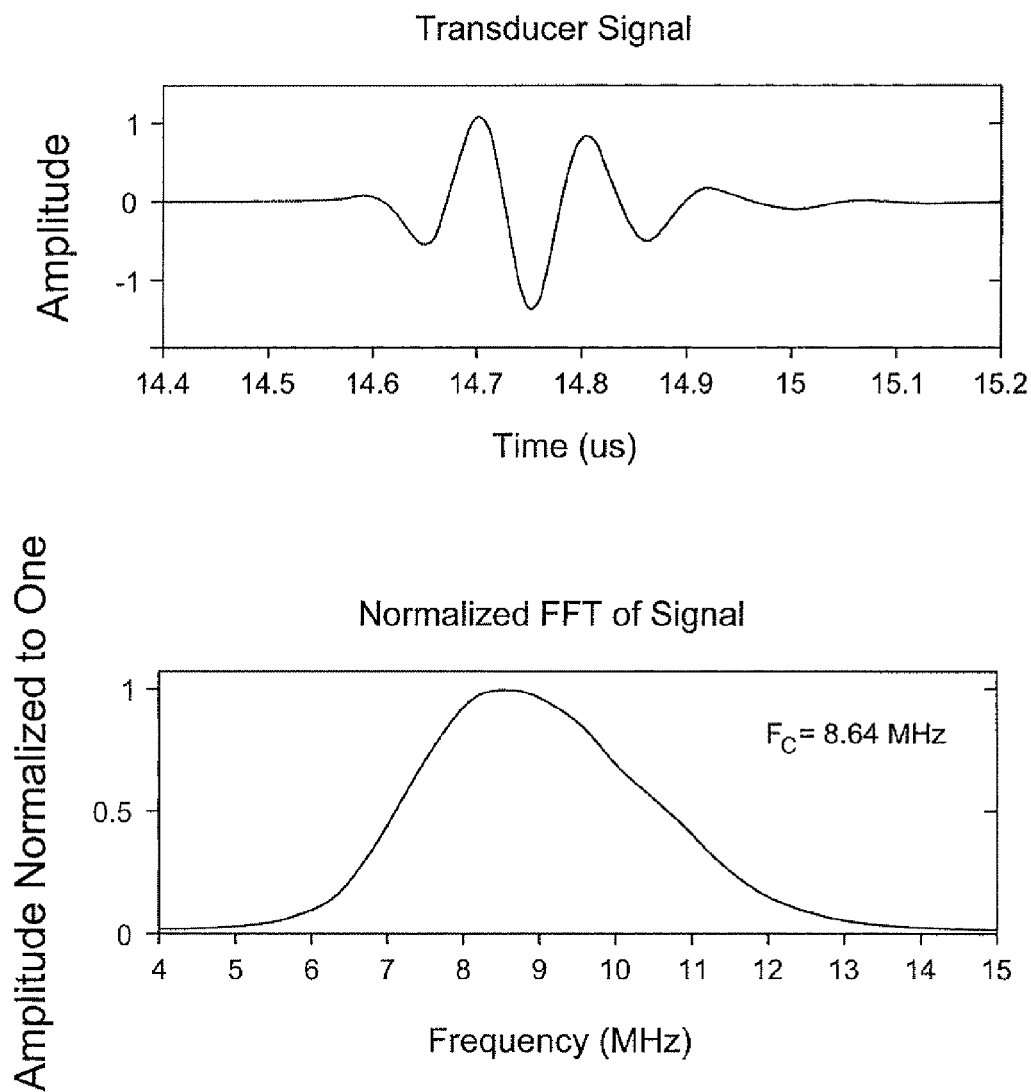
FIG. 5 is a chart showing a transducer signal and a normalized fast Fourier transform of a transducer signal according to an embodiment of the present invention.

The HPCM 100 can include an ultrasonic transducer 210 having a center frequency near 2.25-MHz, 5-MHz, 10-MHz, or 15-MHz, for example, to allow broad bandwidth capabilities with less than four cycles, reasonable damping characteristics, and a transmitted signal that is free of noise. These characteristics allow for reflected signals to be short in time, which will prevent multiple wall reflections from overlapping within thin pipe walls. An example of such a signal is shown with reference to the chart in FIG. 5 showing the transmitted signal and corresponding fast Fourier transform (FFT) of signals from a transducer with the foregoing operating characteristics. Embodiments of the present invention including a normal-incidence single-element transducer having a delay line have been shown to operate at a sufficiently high frequency, thereby resolving accurate thickness measurements over the full thickness range of 2 mm to 30 mm and presenting the fewest complications in implementing an autonomous monitoring sensor.

Figure 11:
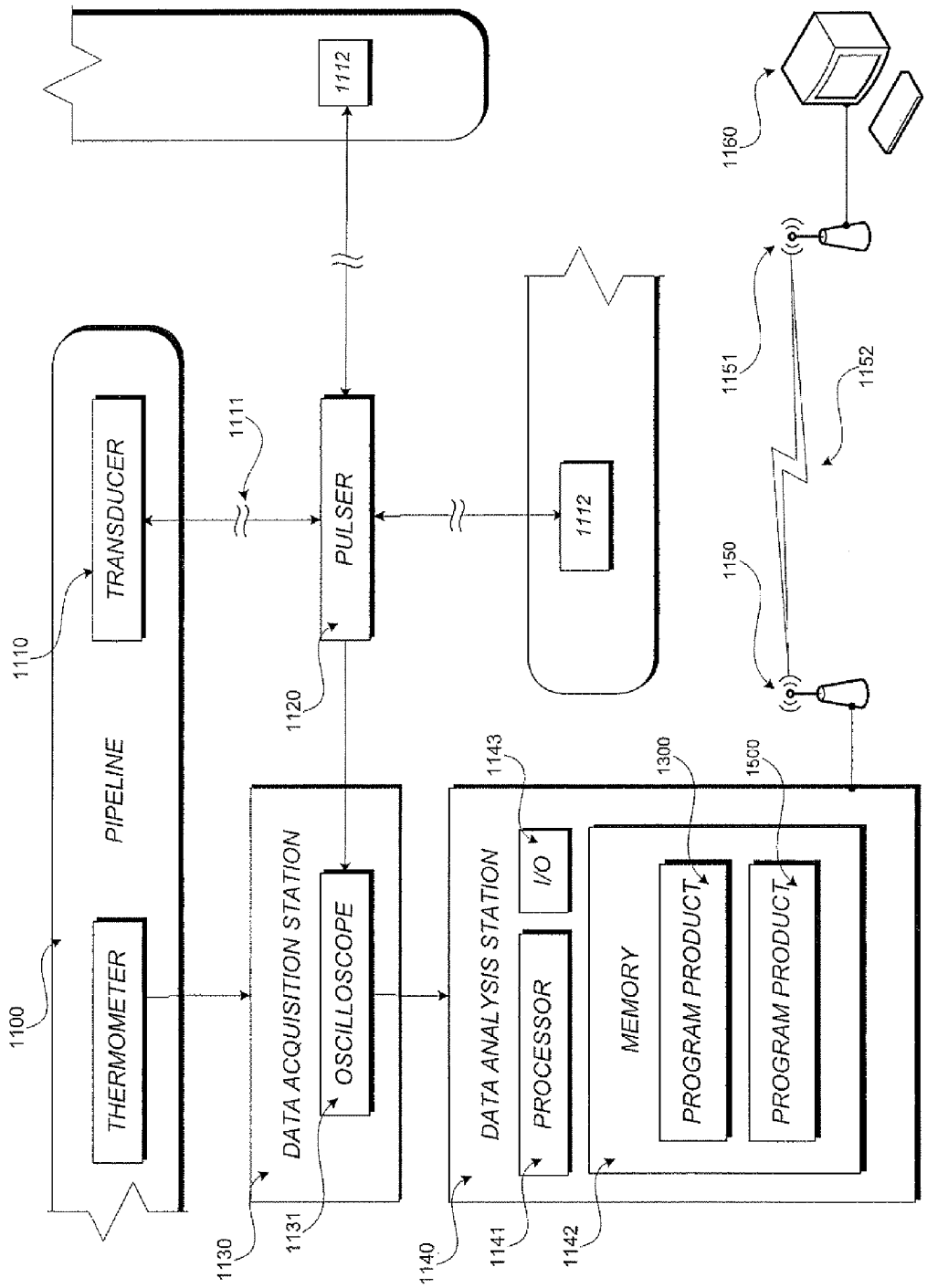
FIG. 11 is a schematic diagram showing a system according to an embodiment of the present invention.

As can be shown with reference to FIG. 11, the ultrasonic transducer 1110 on pipeline 1100 is driven in pulse-echo mode with a pulser 1120, such as a Panametrics 5072 pulser. Signal degradation requires that the cable 1111 between the transducer 1110 and the pulser 1120 be of a length less than or equal to 50 meters. The pulser 1120 must be capable of driving multiple transducers 1112, including approximately twenty (20) transducers. A local measurement system comprises the pulser 1120, a data acquisition system having an oscilloscope 1131, and an autonomous data analysis station 1140. The resulting waveforms are be collected with the oscilloscope 1131, such as a Tektronix TDS 2024B oscilloscope, and the collected waveforms are be analyzed using autonomous computer program products 1300 or 1500, which can be, for example, functions written in MATLAB, executed by a processor 1141 on a monitoring system 1140 having an input/output unit 1143 connecting to the oscilloscope 1131 and a wireless network interface 1150 for connecting with a base station 1160 over a wireless communications network 1152 such as a GSM telecommunications network (Global System for Mobile Communications), which also has a wireless network interface 1151. The base station 1160 can be a computer including software for controlling multiple local systems and executing user-driven data-analysis software. Human users at the base station 1160 can configure and control the local stations through wireless communications 1152. In one embodiment as illustrated in FIG. 11, data analysis station 1140 is connected in a local environment with the data acquisition station 1130, pulser 1120 and transducer 1110. In other embodiments, however, data analysis station 1140 can be connected remotely, for example, using one or more wireless network interfaces (not pictured) to connect the data acquisition station 1130 and the data analysis station 1140 to a wireless communications network, such as wireless communications network 1152. Positioning the data analysis station 1140 remote from the data acquisition station 1130 advantageously allows one data analysis station 1140 to interface with a plurality of data acquisition stations 1130, including at a plurality of remote sites.

As can be shown with reference to FIG. 11, data analysis station 1140 includes a processor 1141, which can be or include one or more microprocessors, microcontrollers, and other analog and/or digital circuit components configured to perform the functions described herein. The processor 1141 is the "brains" of the data analysis station 1140, and as such executes computer program product or products and works in conjunction with the I/O 1143 to direct data to a non-transitory memory 1142 and to send data or commands from the non-transitory memory 1142 to a database, a network interface, and peripherals or installed components. The processor 1141 can be any commercially available processor, or plurality of processors, adapted for use in or with the data analysis station 1140, e.g., an Intel® Xeon® multicore processors, Intel® micro-architecture Nehalem, and AMD Opteron™ multicore processors. As one skilled in the art will appreciate, processor 1141 can also include components that allow the data analysis station 1140 to be connected to a base station terminal 1160, as will be understood by those skilled in the art, having a keyboard or other peripherals that would allow a user to directly or indirectly access the processor 1141 and non-transitory memory 1142 through the remote base station terminal 1160.

As can be shown with reference to FIG. 11, data analysis station 1140 further includes a non-transitory memory 1142 or more than one non-transitory memory. Non-transitory memory 1142 is configured to store a computer program product or products comprising instructions for execution on the processor 1141. Non-transitory memory 1142 includes both non-volatile memory, e.g., hard disks, flash memory, optical disks, and the like, and volatile memory, e.g., SRAM, DRAM, and SDRAM as required to support embodiments of the instant invention. As one skilled in the art will appreciate, though the non-transitory memory 1142 is depicted on, e.g., a motherboard, of the data analysis station 1140, the non-transitory memory 1142 can also be a separate component or device, e.g., flash memory, connected to the data analysis station 1140 through the I/O 1143. For example, user at the base station 1160 can access applications and computer program products stored on the non-transitory memory 1142 and run on the processor 1141. As one skilled in the art will understand, the program product or products, along with one or more databases, data libraries, data tables, data fields, or other data records can be stored either in non-transitory memory 1142 or in separate non-transitory memory 1142, for example, associated with a storage medium, positioned in communication with the data analysis station 1140 through the I/O 1143.

Figure 6:
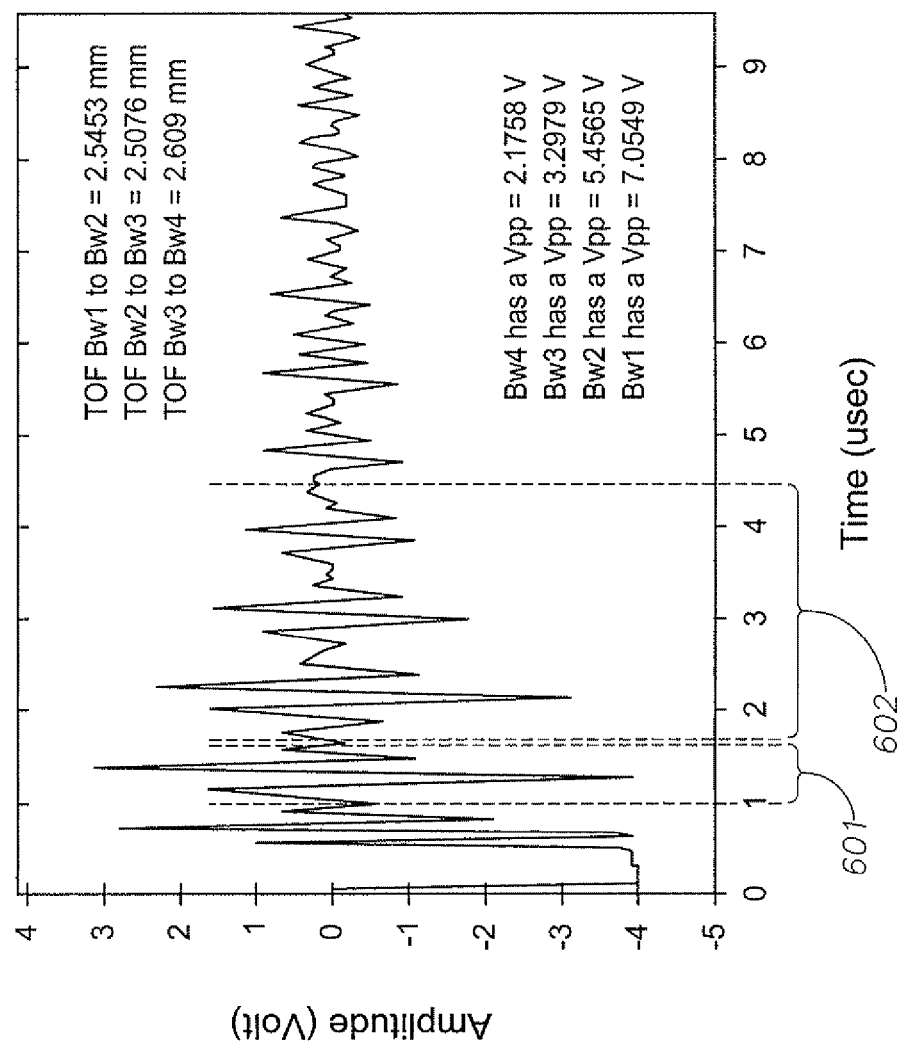
FIG. 6 is a chart showing a transducer signal according to an embodiment of the present invention.
Figure 13:
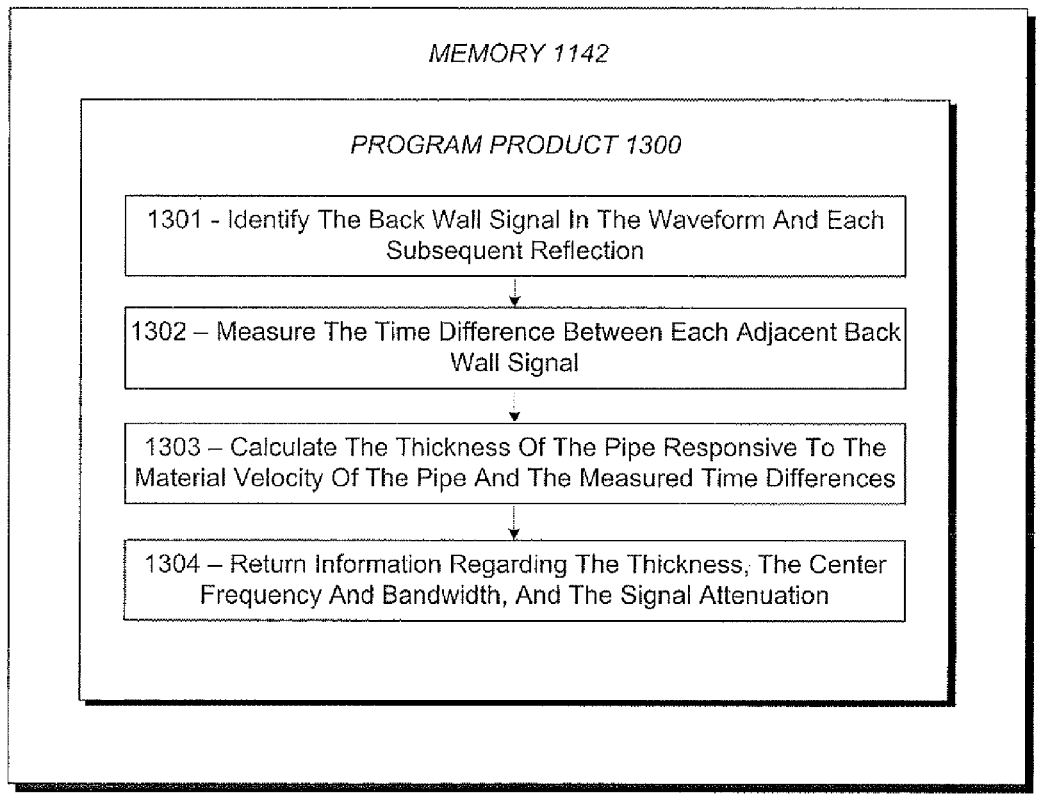
FIG. 13 is a schematic diagram and flowchart showing computer program product and computer-implemented methods according to an embodiment of the present invention.

As can be shown with reference to FIG. 13, such computer program product functions report the thickness of the measured test sample by first identifying 1301 the back wall signal in the waveform and each subsequent reflection and then measuring 1302 the time difference between each adjacent back wall signal. The time difference measurement 1302 can be conducted either through cross correlation of adjacent back wall signals or by a peak detection algorithm. The measured time differences can be used to calculate 1303 the thickness of the pipe 101 based on the material velocity of the pipe 101. Functions can also return 1304, for example, information regarding the center frequency and bandwidth of the back wall signal, as well as the signal attenuation between each back wall. An example of the resulting annotated waveform can be shown with reference to FIG. 6, which shows the waveform output of such a function. The first identified back wall is section 601, and subsequent reflections are in section 602. The function reported a material thickness of 2.55 mm (actual thickness was 2.54 mm). The signal bandwidth ranged between 1.3 MHz and 6.7 MHz, with a center frequency of 3.9 MHz and the average attenuation was 1.7 dB between reflections.

Figure 7:
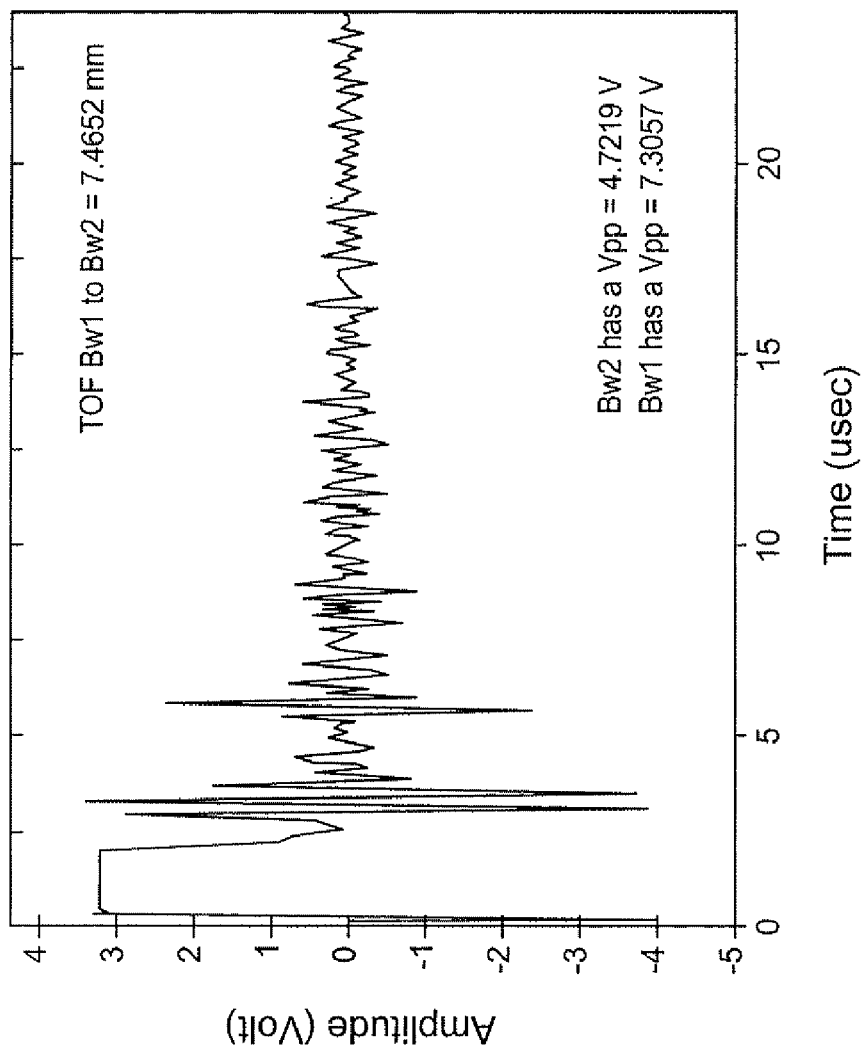
FIG. 7 is a chart showing a transducer signal according to an embodiment of the present invention.

Testing of the HPCM 100 having an ultrasonic transducer 210 having center frequency near 2.25-MHz suggests that the 2.25-MHz transducer disadvantageously provides for noisy collected waveforms and for limited detection of clear back-wall signals. In particular, the 2.25-MHz transducer provides for limited resolution of back wall signals from the initial pulse where the thickness of pipe 101 is small; and likewise, second reflections can become convoluted with the first reflections. An exemplary thickness measurement recorded with the 2.25-MHz transducer on a 7.62-mm thick sample is shown with reference to FIG. 7.

Figure 8:
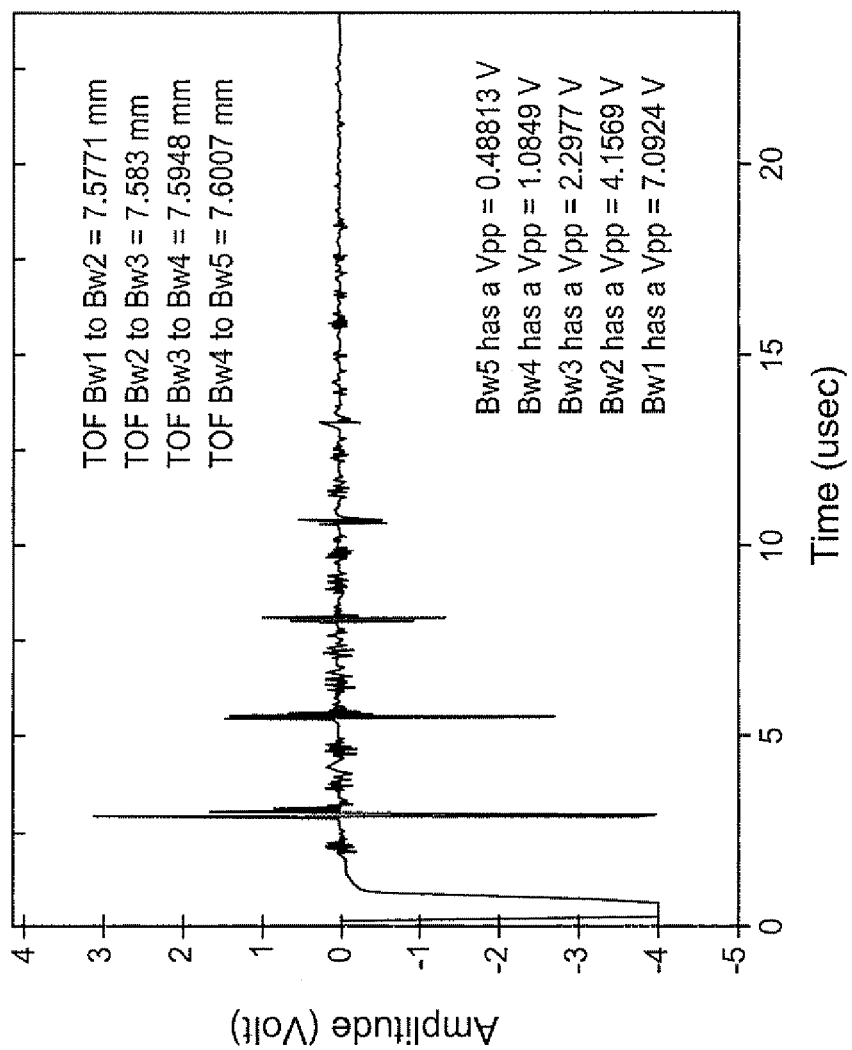
FIG. 8 is a chart showing a transducer signal according to an embodiment of the present invention.

Testing of the HPCM 100 having an ultrasonic transducer 210 having center frequency near 5-MHz or near 10-MHz suggests, in contrast to the 2.5-MHz transducers, that the 5-MHz transducers and 10-MHz transducers advantageously provide for clear back-wall reflections and multiple clear detectable reflections where the thickness of the pipe 101 ranges between 12.7 mm and 2.5 mm. By way of example, FIG. 8 shows an exemplary thickness measurement conducted on a 7.62-mm thick steel block with a 10-MHz transducer where multiple back wall signals are detected and the noise level is low. Accordingly, tests of the HPCM 100 suggest that a single-element longitudinal transducer between the frequency of 5-MHz and 10-MHz would be capable of making pipe thickness measurements within the provided range of 2 mm to 30 mm, and at an accuracy of ±0.5 mm.

Figure 14:
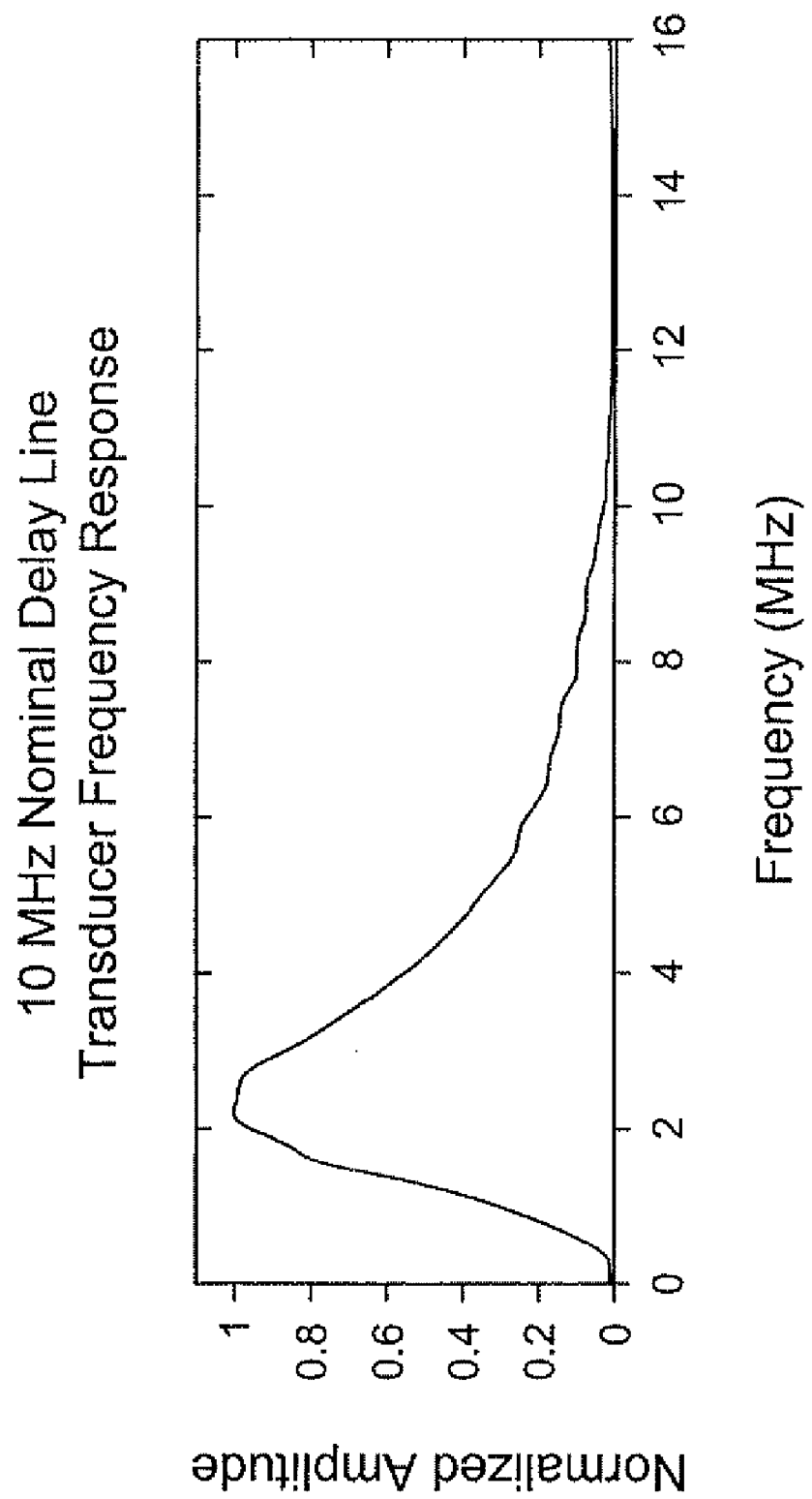
FIG. 14 is a chart showing a frequency response of a transducer according to an embodiment of the present invention.
Figure 15:
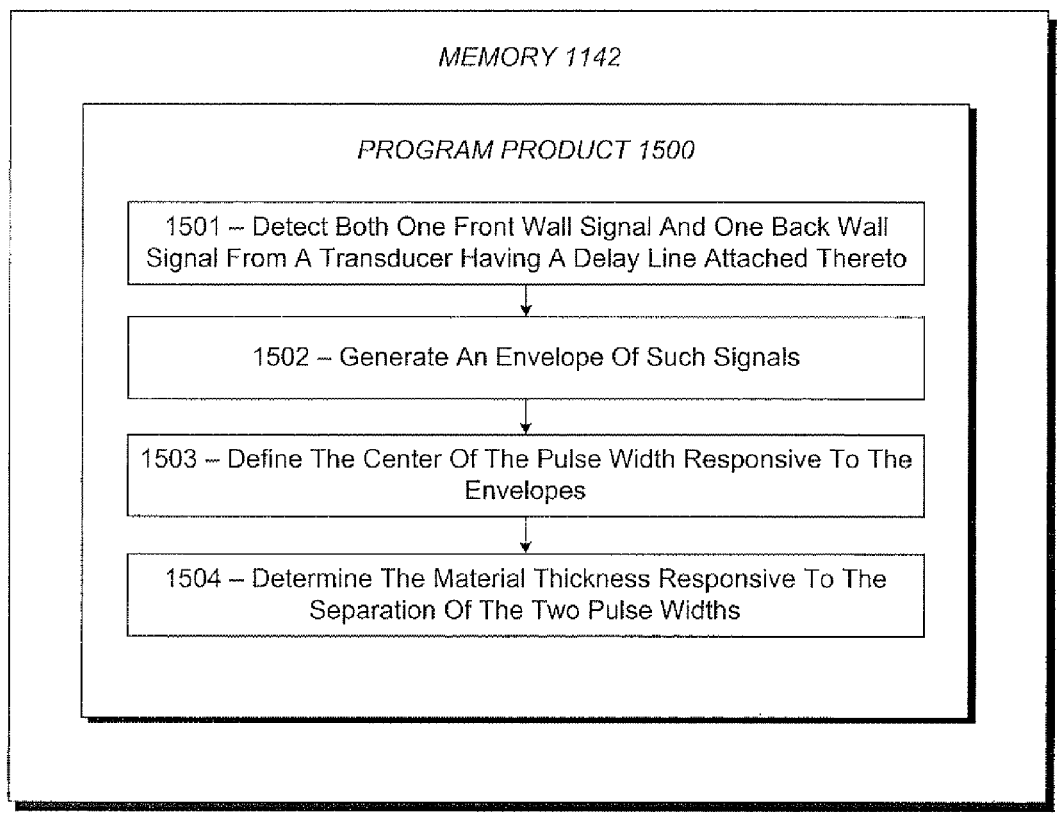
FIG. 15 is a schematic diagram and flowchart showing computer program product and computer-implemented methods according to an embodiment of the present invention.

Testing of the HPCM 100 having an ultrasonic transducer 210 being a 10-MHz, 9.5 mm diameter transducer attached to a 15-mm long Rexolite delay line suggests that the center frequency of the transmitted signal can be significantly attenuated. For example, without the delay line, the center frequency of the transmitted signal is approximately 8 MHz, and the bandwidth is fairly symmetric on either side of the center frequency. With the delay line incorporated, the center frequency measures 2.25-MHz, and the bandwidth trails into the higher frequency range. By way of reference to FIG. 14, the frequency response of the 10-MHz normal-incidence transducer with the 15-mm-thick Rexolite delay line installed on the transducer using a film of epoxy is shown. Where the delay line attached to the transducer detects both of one front wall signal and one back wall signal, waveform analysis is required to generate an envelope of each of those signals and then define the center of the pulse width responsive to those envelopes. The separation of the two pulse widths can then be used to estimate material thickness. Because the pulse widths of the signals are used, information regarding the signal peaks is unnecessary and waveforms having higher sensitivity settings can be used. Accordingly, this measurement solution presents an alternative to cases where looking for multiple back wall reflections in a waveform presents an unreliable approach to making wall thickness measurements.

On a typical pipeline, the transducer 210 is expected to experience variations in temperature between 0° C. and 120° C. due to climate conditions. The transducer must be able to both operate for long periods of time at temperatures up to 120° C. and return thickness readings with an accuracy of ±0.5 mm for pipe walls up to 30 mm thick regardless of the pipe temperature. Further, testing of the HPCM 100, at room temperature (22° C.) on a pipe 201 made of 1018-carbon steel, which has a rate of velocity change of $8.015*10-4$ mm/μs/° C., suggests that the thickness change of the pipe 201 material within the stated range of operating temperatures will only rarely result in the error exceeding the tolerable error of 0.5 mm. For example, the velocity of 1018 carbon steel at room temperature (22° C.) was measured to be approximately 5.856 mm/μs, and a pipe 201 having the maximum allowable pipe thickness of 30 mm will experience an apparent thickness change of 0.41 mm between a waveform acquired at room temperature and a waveform acquired at the maximum specified temperature. At the greatest pipe thickness, this change can exceed the tolerable error specified in addition to the other measurement errors inherent to the system. Accordingly, when achieving a specified accuracy is critical, it may be necessary to include a temperature measurement capability on the thickness measurement system so that the waveform analysis accounts for temperature variations. If the change in the material velocity of the pipe, as a function of temperature, is small enough in carbon steels, the variation of apparent thickness due to temperature change can be ignored. Tests have shown, for example, that in the case of the maximum pipe thickness of 30 mm, an apparent thickness change of 0.41 mm will occur between a waveform acquired at room temperature and a waveform acquired at the maximum specified temperature.

The transducer 210 is able to produce consistent measurements in an outdoor environment where the transducer is fixed to the pipe 201 according to embodiments of the present invention. As can be shown with reference to FIG. 2, the HPCM 100 allows the ultrasonic transducer 210 to be fixed in a position on the outer pipe wall 202 so that the transducer base 212 mechanically bonds to the outer pipe wall 202 at a first mounting location 261. The transducer base 212 includes the elements of the ultrasonic transducer 210 for receiving and transmitting. The bond between the transducer base 212 and the outer pipe wall 202 at the first mounting location 261 can be formed using an epoxy, which also functions as an ultrasonic couplant or coupling media, to enhance the communication of ultrasonic energy between the outer pipe wall 202 and the ultrasonic transducer 210 by eliminating air gaps. The epoxy can be, for example, 3M® Scotch-Weld® DP125 epoxy. The epoxy allows for an effective bond between the transducer base 212 and the outer pipe wall 202 where the transducer base 212 is positioned substantially tangential to the outer pipe wall 202 at the first mounting location 261. In certain embodiments, the transducer base 212 can be flat in order to accommodate an outer pipe wall 202 having any diameter of a range of diameters, or potentially, for mounting to a flat surface. So that an effective bond between the transducer base 212 and the outer pipe wall 202 is achieved, and so that effective ultrasonic transmissions are achieved between the transducer base 212 and the outer pipe wall 202, the HPCM 100 accommodates a pipe 201 having an outer diameter of the outer pipe wall 202 that is greater than or equal to six (6) inches.

In embodiments of the present invention having a delay line, the delay line bonds to the transducer 210 between the transducer 210 and the pipe 201. In embodiments having a delay line, it is the base surface of the delay line (not pictured) that is mechanically bonded to the outer pipe wall 202 at the first mounting location 261. The top surface of the delay line and the base surface of the ultrasonic transducer are mechanically bonded 920 as shown with reference to FIG. 9. The described structure of embodiments of the invention herein will be understood to apply to either a transducer base 212 or the base of a delay line being mechanically bonded at the first mounting location. The delay line, which can be, for example, approximately 0.625 inches in diameter and 0.5 inches in thickness bonds to the transducer with a thin film of epoxy. The transducer having the delay line attached is structurally bonded to the outer pipe wall 202 at the first mounting location 261 as described herein. A transducer and bonded delay line is shown with reference to FIG. 9.

As can be shown with reference to FIG. 2, the transducer 210 can be further bonded to the pipe 201 using a fixture 200 called a Transducer Hold Down Fixture ("THDF"), which is part of the HPCM assembly. The THDF 200 provides a rigid, but adjustable, frame for mounting the HPCM 100 on a pipe having any diameter within a range of diameters. In addition to the epoxy bond between the transducer 210 (or the delay line if so equipped) and the pipe 201 at a first mounting location 261, the THDF 200 provides two additional bonds between the HPCM 100 and the pipe 201 at a second mounting location 262 and at a third mounting location 263. The addition of the bonds at the second mounting location 262 and at the third mounting location 263 allows the use of a larger, more accurate transducer 210 and further allows the use of a delay line (i.e., the transducer having a delay line is necessarily taller than the transducer alone). For example, larger transducers or transducers with delay lines are subject to lateral force that might defeat an epoxy bond being the sole means of bonding the transducer to the pipe. The bonds at the second mounting location 262 and at the third mounting location 263, for example, provide added support to the bond at mounting location 261 with respect to increased torques created by lateral forces acting on the lever-arm provided by a larger transducer or a transducer using a delay line.

As is shown in FIG. 2, the transducer 210 is attached to the THDF 200 at a part of the THDF referred to as the transducer housing cross-member 270. The transducer 210 attaches to the housing cross-member 270 using a transducer housing clamp 213. In other embodiments, the transducer attaches directly to the transducer housing cross-member 270, for example, using a male-threaded transducer that screws into a socket in a female-threaded transducer housing cross-member 270. A transducer housing cross-member is shown with reference to plate 330 at FIG. 3C, and the transducer housing clamp is shown with reference to clamp blocks 340 and 350 in FIGS. 3D-3E. As is shown with reference to FIGS. 2 and 3D-3E, the transducer 210 is housed in the space between semi-cylindrical channels 343 and 353 of clamp blocks 340 and 350 (the transducer housing clamp 213 shows the clamp blocks 340 and 350 as an assembled unit of both blocks). As can be shown with reference to FIG. 2, the transducer 210 is substantially surrounded by the transducer housing clamp 213 (the transducer 210 continuing with dotted lines down to the outer surface 202 of the pipe 201), which protects the transducer 210 and the delay line (not pictured) from environmental forces.

Figure 12A:
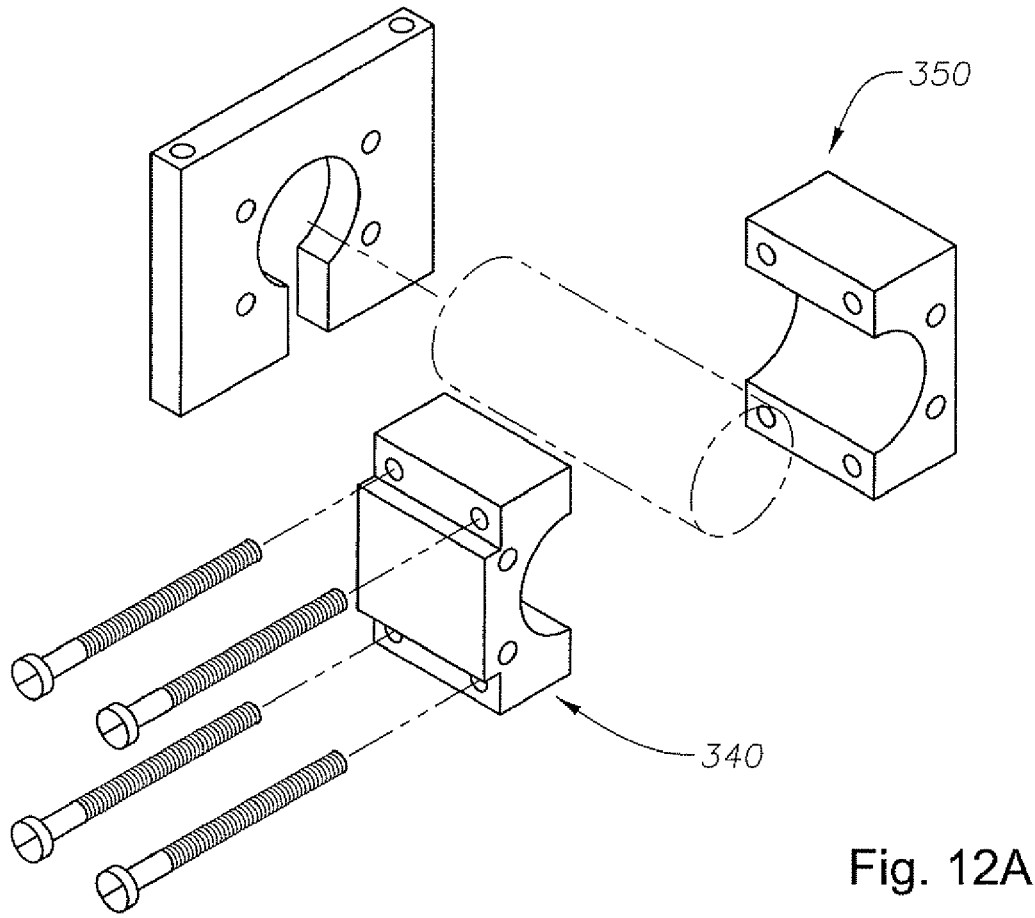
FIGS. 12A-12B are schematic drawings showing component parts of an assembly according to an embodiment of the present invention.
Figure 12B:
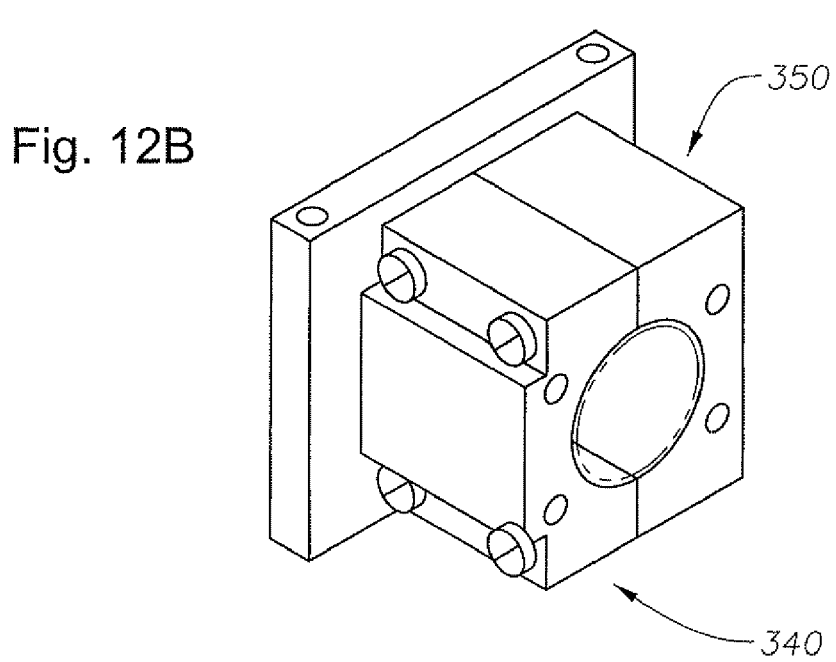

As is shown with reference to FIGS. 3D-3E, clamp blocks 340 and 350 include sockets 349 and 359 so that clamp blocks 340 and 350 can be clamped around transducer 210 by screwing together clamp blocks 340 and 350 with screws running through sockets 349 and 359. Further reference may be made to FIGS. 12A-12B, which show the clamp blocks 340 and 350 being screwed together. When transducer 210 is clamped within clamp blocks 340 and 350, the transducer base of transducer 210 (or the base of the delay line) should be even or flush with the base of transducer clamp blocks 340 and 350. Flush fitment prevents the transducer from "rocking" when placed on the pipe, which could happen if the transducer surface or the delay line protrudes past the clamp base surface. Also, flush fitment further prevents bubbles from forming in the recess when the transducer is epoxied to the pipe surface and resultant attenuation of the ultrasonic energy, which could happen if there is a recess between the transducer base or the delay line and the clamp base surface.

Clamp blocks 340 and 350, having transducer 220 clamped therein, are be attached to the cross-member 330, for example, using slider screws 214 running through sockets 333-336 of the cross-member 330 and sockets 341-342 of clamp block 340 and sockets 351-352 of clamp block 350. In some embodiments, spring tension may be provided for biasing the ultrasonic transducer in the direction of the outer pipe wall. In such embodiments, as can be shown in FIG. 10, one or more slider screws 214 are surrounded by a substantially coaxial coil spring 215 between the cross member 330 and the clamp blocks 340 and 350. The cutout 339 in the cross-member 330 allows the top of the transducer 210 to protrude from the transducer housing cross-member 270 so as to accommodate transducers of various sizes (including transducers having delay lines attached thereto). In alternate embodiments, the cutout 339 in the cross-member 330 allows the top of the transducer 210 to protrude from the transducer housing cross-member 270 so as to accommodate various configurations where thickness of clamp blocks 340 or 350 can be reduced, causing the transducer to protrude from the cutout 339. The size of the clamp blocks 340 and 350 can be reduced, for example, to reduce the size of the THDF 200 so as to reduce the effect of environmental forces on the HPCM 100 or to allow fitment on pipes having a small diameter.

As can be further shown with reference to FIG. 2, the transducer housing cross-member 270 not only attaches to the transducer 210, but also to a first tower 220 and a second tower 230, which, as are described further herein, provide further support to the HPCM 100 in bonding the HPCM 100 to the pipe 201 at two additional locations. The first tower 220 and the second tower 230 flank either side of the transducer 210 and the transducer housing cross-member 270 so that the first tower 220, the transducer 210, and the second tower 230 are aligned along a common arc along the outer wall 202 of the pipe 201. As can be shown with reference to FIG. 2 as well as to FIGS. 3A-3B, the cross-member 330 is attached to both of the first tower 220 and the second tower 230 by hinge pins 271 and 272 that attach to the cross-member 330 by enclosure in hinge pin sockets 331 and 332 at the distal ends of the cross-member 330. As can be shown with reference to FIG. 2, towers 120 and 130 include hinge tracks 223 and 233 to receive hinge pins 271 and 272. Hinge pins 271 and 272 are be free to rotate within the hinge pin sockets 331 and 332 and in hinge tracks 223 and 233, which allows the THDF 200 to be an adjustable, articulating assembly. Hinge pins 271 and 272 are, for example, slider screws that can be tightened, for example, where hinge pins 271 and 272 each have one or more threaded ends and include threaded fasteners, such as a nut, so as to restrict the abilities of hinge pins 271 and 272 to rotate within the hinge pin sockets 331 and 332 or tracks 223 and 233, thereby creating a rigid structure. Tracks 223 and 233, as are shown with reference to FIG. 2, are elongated and extend out along the same direction as either distal end of the cross-member 270, thereby allowing the hinge pins 271 and 272 to slide within the tracks 223 and 233, which causes the distance between the cross-member 270 and either tower 220 and 230 to be adjusted. Tightening of hinge pins 271 and 272 also restricts the abilities of the hinge pins 271 and 272 to slide within the tracks 223 and 233. Accordingly, hinge pins 271 and 272 allow the articulated shape of the THDF 200 to be adjusted with respect to the angles of the towers 120 and 130 as well as with respect to the placement of towers 120 and 130, thereby allowing multiple configurations for pipes having divergent diameters.

A first tower 310 and a second tower 320 can be shown with reference to FIGS. 3A and 3B. For the purpose of describing both the first tower 310 and the second tower 320, reference can be made to either tower, which can be identical in design and construction as can be shown with reference to towers 310 and 320 in FIGS. 3A and 3B. Accordingly, numbered references to FIG. 3A also apply to FIG. 3B, though towers 310 and 320 should be understood to be two separate towers.

Tower 310 includes a ledge 314 on the upper portion of the tower 310, as can also be shown with reference to ledge 279 in FIG. 2, that is positioned inwards in the THDF 200 as can also be shown with reference to HPCM 100 in FIG. 2. Referring back to FIG. 3A, track 223 is positioned on tower 310 at least partially on the ledge 314 portion. As can be shown with reference to FIG. 2, ledge portion 314, having the track 223 positioned thereon, and extending inwards from tower 220 allows tower 220 to have a range of freedom in rotating about hinge pin 271 so as to avoid contact between the tower 220 and the transducer 210 near the outer surface 202 of the pipe 201, for example, when the THDF 200 is adjusted to fit a particular diameter of pipe 200. Returning to FIG. 3, certain embodiments provide a ledge 314 portion having a central cutout 313, which provides a relief space in ledge 314 so that the tower 310 can have a range of freedom rotating about hinge pin 271 so as to avoid contact between tower 310 and the transducer 210, for example, when the THDF 200 is adjusted to fit a particular diameter of pipe 200. Although ledge 314 is shown as having an open central cavity 317, central cavity can also be a closed hollow space or ledge 314 can be a solid mass. Track 223, in embodiments having a open central cavity 317, can include two track cutouts 311, as can further be shown with reference to FIG. 3A.

The portion of tower 310 below the ledge 314 can be shown with reference to tower foot 316. Tower foot 316 has a magnet cutout 315 as can be shown with reference to FIG. 3A. In certain embodiments, the magnet cutout 315 is a hollow channel of tower foot 316 at the base of tower foot 316 where the magnet 224 is installed substantially flush with a portion 318 of the base of tower foot 316 wholly or partially surrounds the magnet cutout 315, as can be shown with reference to FIG. 2. In alternate embodiments, there may be no magnet cutout 315, and the magnet 224 has the same length and width as the tower foot 316 and is mounted flush with the sides of tower foot 316. In such an embodiment, the magnet 224 may be screwed onto the tower foot 316. In other embodiments, the magnet 224 is completely enclosed in a hollow portion of tower foot 316 so that the magnet 224 is fully enclosed by the tower 330 and is capable of magnetic bonding to the pipe 201 without having physical contact between the magnet 224 and the pipe 201. In certain embodiments, the magnets are protected from the environment by the tower material as well as by an epoxy. Although the walls 318 of the tower foot 316 are shown surrounding magnet 224 on only two sides in FIG. 3A, other embodiments allow the walls 318 of tower foot 316 to completely surround magnet 224 on four sides. Walls 318 of tower foot 316 that surround magnet 224 serve to shield transducer 210 from interference with magnet 224 as well as to protect magnet 224 from corrosion or erosion from environmental factors or forces. In certain embodiments, towers 310 and 320 are constructed of a high-durability and corrosion-resistant plastic or composite, such as polyvinyl chloride (PVC) or fiberglass-reinforced nylon. Certain embodiments further include lamination with a permalloy film to shield transducer 210 from the magnetic field of magnets 224 and 234. The magnets 224 and 234 are preferably a high-strength neodymium magnets or ferrite magnets.

In certain embodiments, both the base of the magnet 224 and the base of tower foot 316 are flat and are flush, providing a flat base surface that accommodates a wide range of diameters of the outer pipe surface 202 of the pipe 201. In other embodiments, the base of the magnet 224 and the base of tower foot 316 are flat, but the base of the magnet 224 is recessed from the base of tower foot 316 to better conform to a more narrow range of diameters of the outer pipe surface 202 of the pipe 201. In other embodiments, the magnitude of the recess is adjustable, for example, using spring tension, to better conform to a wider range of diameters of the outer pipe surface 202 of the pipe 201. In other embodiments, the base of the magnet 224 and the base of the tower foot 316 are curved to best conform to a specific diameter of the outer pipe surface 202 of the pipe 201.

As can be shown with reference to FIG. 2, the towers 220 and 230 are attached to the cross-member 270 by hinge pins 271 and 272. Before hinge pins 271 and 272 are tightened to create a rigid fixture, towers 220 and 230 are rotated about hinge pins 271 and 272, and towers 220 and 230 are slid inward or outward, as the case may be, from the transducer along hinge pins 271 and 272, which ride inside of tracks 223 and 233. The "positioning" or "position" of towers 220 and 230 with relation to the THDF 200 refers to both the rotating (angle) and the sliding (distance) of the hinge pins 271 and 272 within the tracks 223 and 233. Accordingly, the position of towers 220 and 230 can accordingly be adjusted responsive to the diameter of the pipe 201. Where the HPCM 100 is to be mounted on a flat surface, the angle of the towers 220 and 230 can be configured so that the base of towers 220 and 230 and the transducer base 212 of transducer 210 (or the base of the delay line, if so equipped) are coplanar. Where the HPCM 100 is to be mounted on a curved surface, such as on the outer surface 202 of a pipe 201, the position of the towers 220 and 230 can be configured so that the base of towers 220 and 230 and the transducer base 212 of transducer 210 (or delay line) exist on a common arc defined by the outer surface 202 of the pipe 201. The base of towers 220 and 230 and the transducer base 212 of the transducer 210 (or delay line) exist on a common arc when, for example, each of the three bases are substantially tangential to the common arc. In particular, the distance of the towers 220 and 230 can be configured with respect to the angle of the towers 220 and 230 so that the bases of towers 220 and 230 do not physically interfere with the transducer base 212 of the transducer 220 (or delay line). For example, pipes having a smaller diameter will require a configuration having a greater angle as well as a greater distance. In the embodiment shown in FIG. 2, tracks 223 and 233 are linear. In other embodiments, tracks 223 and 233 are curved in the same direction as the common arc, as is shown by tracks 311 and 321 in FIGS. 3A and 3B. Such curvature, for example, allows a greater range of movement of the towers and adjustability of the HPCM 100. As shown in FIGS. 2, 3A, and 3B, hinge pins 271 and 272 are received into tracks 223 and 233 at an axis of rotation that is perpendicular to the plane containing the common arc, and accordingly, angle adjustments about the axis of rotation allow the base of towers 220 and 230 to be positioned so that they are substantially tangential to the common arc of the outer pipe wall.

Figure 4:
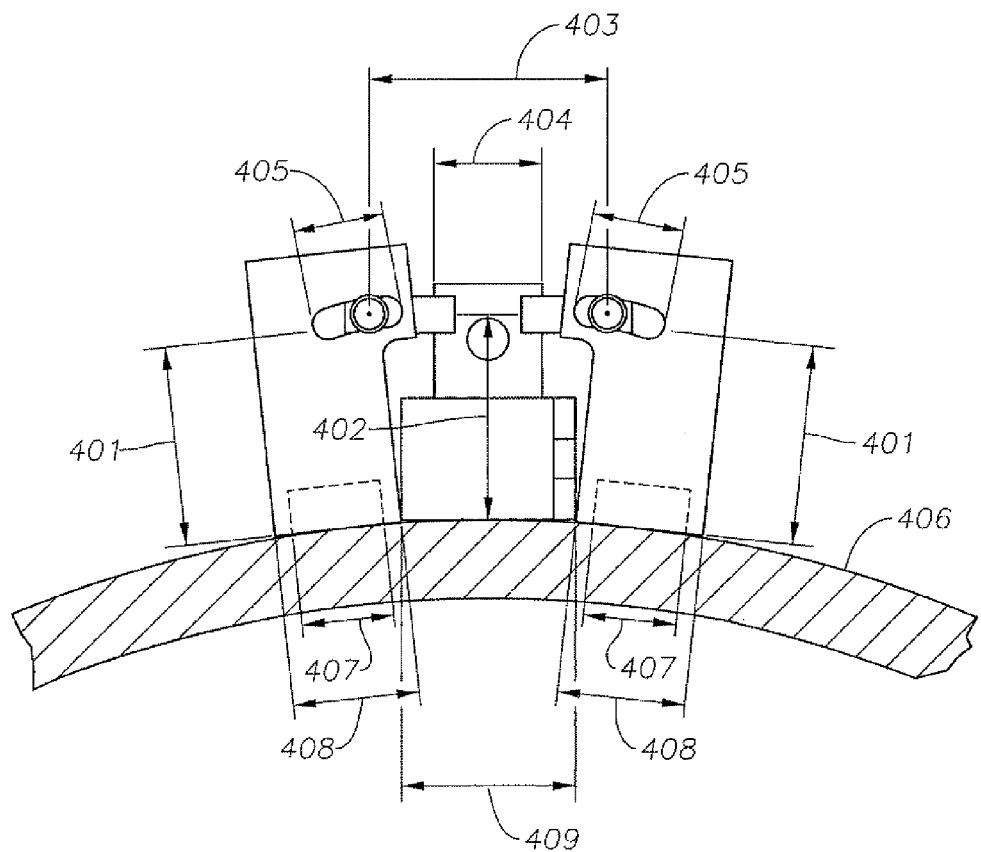
FIG. 4 is a blueprint drawing showing an axial view of an assembly according to an embodiment of the present invention. Measurements are provided in inches first, and in millimeters (mm) in brackets.

With towers 220 and 230 positioned as illustrated in FIGS. 1 and 2, i.e., the bases of towers 220 and 230 and the bases of magnets 224 and 234 being positioned substantially tangential to the outer pipe surface 202 of the pipe 201, the first hinge pin 271 and the second hinge pin 272 can be tightened to prevent further adjustment of the angle and distance of the towers 220 and 230 with respect to the cross-member 270, thereby making the THDF 200 and the HPCM 100 a rigid structure. Accordingly, where the HPCM 100 has been made rigid, the magnets 224 and 234 form a second bond at the second mounting location 222 at the first tower 220 and a third bond at the third mounting location 232 at the second tower 230. The second and third bonds between the HPCM 100 and the pipe 201 thereby provide a clamping force pressing the transducer base 212 of transducer 210 towards the outer pipe surface 202 of the pipe 201, in a radial direction with respect to the pipe 201. The ability of the THDF 200 to be made rigid in a configuration corresponding to the diameter of the outer pipe surface 202 of the pipe 201 allows the forces exerted by the THDF 200 at the second mounting position 222 and the third mounting position 232 to have a direction that is radial with respect to the pipe 201, ignoring any forces due to gravity. That the THDF 200 is rigid and that the forces at the second mounting position 222 and the third mounting position 232 are radial enhances the stability of the HPCM 100 on the pipe 201, allowing the HPCM 100 to withstand greater environmental forces. Moreover, the rigidity of the THDF 200 in any configuration allows the forces at the first bond 212, the second bond 222, and the third bond 232 to be consistent across the THDF 200's range of pipe diameters, including at the extremes. Consistent clamping force across the range of pipe diameters advantageously provides an HPCM 100 wherein the transducer 220 produces consistent measurements across the range of pipe diameters for the THDF 200, and requires no change in calibration or maintenance responsive to the diameter of the pipe 201 on which the THDF 200 is mounted, provided that the diameter of the pipe 201 is within the given diameter range. As can be shown with reference to FIG. 4, an embodiment of a THDF having the level of adjustability for accommodating the transducers described herein, including a delay line, throughout the diameter range (minimum diameter requirement) includes the following dimensions:

| | |
|---|---|
| Height 401 of track 223 from base of tower 220 | 1.253 inches |
| Height 402 of cross-member 270 from base of transducer housing clamp 213 | 1.260 |
| Width 403 between hinge pins 271 of cross-member 270 | 1.500 inches |
| Width (diameter) 404 of ultrasonic transducer 210 | 0.625 inches |
| Width 405 of track 223 | 0.572 inches |
| Minimum diameter 406 of outer pipe wall 202 | 6.000 inches |
| Width 407 of magnet 224 | 0.500 inches |
| Width 408 of tower 220 | 0.750 inches |
| Width 409 of transducer housing clamp 213 | 1.000 inches |

The HPCM 100 is designed to monitor the metal losses in pipes and vessels with a high degree of precision and accuracy at a single location. Because the HPCM 100 can monitor only a small area, the HPCM is designed to be permanently installed at a location where corrosion has already been detected, rather than used as a search tool. The HPCM 100 can be installed at a regularly inaccessible location, and a lead wire can be extended from the HPCM to a remote location for data collection. The lead wire can be extended approximately fifty (50) meters away from the sensor.

Tests have confirmed that a coaxial cable with a length up to 50 m does not affect the thickness measurement. In a typical coaxial cable, each unit length of the cable is noted to contribute some series inductance and some parallel capacitance to the terminating load, which can be interpreted as a series of low pass filters, where each differential length contributes to the order of the low pass filter. From this, it is apparent that higher frequencies will be more heavily attenuated by the coaxial cable, and longer cables will have greater effect on the signal carried thereon. Very long cables could also cause broadening of higher frequency signals. Additionally, the coaxial cable will act as a time-delay line, so longer cables will tend to phase shift the reflected signal relative to the transmitted pulse. Where the only critical measurement for the thickness measurement system is time-of flight, these effects are minimal as long as (1) the reflected signal amplitude remains clearly detectable above the noise level, (2) the transducer center frequency does not become heavily attenuated, and (3) the time difference between two back wall signals, or a detectable front wall and back wall signal, does not shift significantly enough to exceed measurement accuracy specifications.

Tests have confirmed that both the 5-MHz transducer and the 10-MHz transducer are able to return accurate and consistent thickness measurements even at the maximum cable length of 50 m. The same consistency, however, is not provided by the 2.25-MHz transducer (which is at least in part attributable to the high level of acoustic noise and higher signal attenuation observed). Because the back wall multiple reflections of the 2.25-MHz transducers are not significantly larger in amplitude than in the acoustic noise, the noise distorts the multiples thereby reducing the measurement accuracy. Although the 5-MHz and the 10-MHz transducers produce thickness measurements with much greater accuracy, they are also more significantly affected by increasing cable length. The signal attenuation in the sample for both the 5-MHz and the 10-MHz transducers was typically around 2 to 3 dB. In contrast, tests have shown that the 5-MHz signal experienced 0.09 dB/m of attenuation in the cable and that the 10-MHz transducer experienced 0.11 dB/m attenuation. Accordingly, significantly smaller signal amplitudes result at the maximum cable length. This attenuation, however, is tolerable because even at the maximum cable length, reflections acquired on the 5-MHz and 10-MHz transducers are much larger in amplitude than the noise level.

Tests have also demonstrated the tendency of the coaxial cable to act as a low pass filter. Regardless of the length of the cable, the center frequency of the 2.25-MHz and the 5-MHz transducers largely remain unaffected. The center frequency of the 10-MHz transducer, however, can drop by nearly 1.6 MHz from the acquisition with the shortest cable length to the acquisition with the longest cable length. Accordingly, coaxial cable having low capacitance is required where transducers having a center frequency of 10-MHz are used. For functions measuring thickness using time of flight, it is important to note that a time shift does occur with respect to longer cables. Tests have confirmed that a time delay of approximately 10 nanoseconds results for each additional meter of cable, independent of transducer frequency. For example, a 50 m cable adds 0.5 µs between the initial pulse and all subsequent signals, which correlates directly to the time it takes for the electrical signal to travel up and down the length of the cable. Where signal processing functions do not capture multiple back wall signals or a back wall and a front wall reflection, time delay must be accounted for in the thickness measurement functions. As long as the selected transducer can capture either multiple back wall reflections or a back wall and a front-wall reflection, adding a long cable between the transducer and the pulser will not produce a measurement error in excess of the error tolerances.

Embodiments of the invention using a single-element, normal-incidence transducer, that is attached to a delay line, require calibration. Calibrating the transducer, for example, can include using an ultrasonic flaw detector machine having a current calibration certification to establish the base line and monitoring readings. Initial calibration can be performed using a step wedge calibration block which will allow finding the parameters for further readings. Calibration includes the steps of (i) finding the main pulse or main bang of the transducer (electronic zero) by means of the delay control or its equivalent; (ii) inputting the theoretical longitudinal velocity for steel (5900 m/s) as a reference; (iii) adjusting as necessary the range control to get on the screen both main pulse and first delay line echo, the latest corresponding to the wedge extreme edge which is attached to the transducer; (iv) placing the transducer on a step of the calibration block such that the first back-wall echo after the delay line indication can be known; and (v) adjusting frequency, damping, or their equivalents in order to obtain a clear and steady echo peak and signal to noise ratio. After the calibration process is carried out, calibrated velocity can be checked to be close to the theoretical value (5900 m/s), with a value being +/−50 m/s suggesting a mistake during the calibration process. The calibration is valid for only the thicknesses contained in the range of the steps chosen for the calibration process.

Because calibration is to be performed without paint and on a flat surface, it is necessary to compensate for paint thickness and curvature effects. For example, the HPCM 100 can be placed on the part to be inspected, and a signal can be obtained from the first back wall echo. Further, the peaks of the first and second echo can be compared (reading of echo 2−reading echo 1). Where the difference exceeds 0.2 mm, the zero (μs) can be changed to modify the entry point of the wave (mechanical zero)—larger to lessen the reading or smaller to increase the reading. The zero can be changed until the reading from the first echo and the reading corresponding to the difference between first and second echoes are the same.

The foregoing has broadly outlined certain objectives, features, and technical advantages of the present invention and a detailed description of the invention so that embodiments of the invention may be better understood in light of features and advantages of the invention as described herein, which form the subject of certain claims of the invention. It should be appreciated that the conception and specific embodiment disclosed may be readily utilized as a basis for modifying or designing other structures for carrying out the same purposes of the present invention. It should also be realized that such equivalent constructions do not depart from the invention as set forth in the appended claims. Terms referred to herein and in the claims as "first," "second," "third," and so on should not be construed to incorporate an ordinal element, as those modifiers are intended only to differentiate elements having similar names. The novel features which are believed to be characteristic of the invention, both as to its organization and method of operation, together with further objects and advantages is better understood from the following description when considered in connection with the accompanying figures. It is to be expressly understood, however, that such description and figures are provided for the purpose of illustration and description only and are not intended as a definition of the limits of the present invention.

That claimed is:

1. A high-precision corrosion monitoring sensor assembly to be permanently mounted on an outer pipe wall of a pipe for measuring remaining wall thickness of the pipe, the pipe having any diameter within a preselected range of diameters, the high-precision corrosion monitoring sensor assembly comprising:
   an ultrasonic transducer for measuring remaining wall thickness of a pipe, a first base of the ultrasonic transducer being positioned to bond to an outer pipe wall of the pipe at a first mounting location when the first base is positioned substantially tangential to the outer pipe wall at the first mounting location; and
   an adjustable transducer hold down fixture being for housing the ultrasonic transducer and for bonding the ultrasonic transducer to the outer pipe wall at a second mounting location and at a third mounting location, the adjustable transducer hold down fixture including:
      a cross-member attached to the ultrasonic transducer, a first distal end of the cross-member having a first pivot pin attached thereto, a second distal end of the cross-member having a second pivot pin attached thereto, a first axis of rotation about the first pivot pin being substantially parallel to a second axis of rotation about the second pivot pin,
      a first tower for supporting the adjustable transducer hold down fixture, a second base of the first tower being magnetic and positioned to bond to the outer pipe wall at the second mounting location when the second base is positioned substantially tangential to the outer pipe wall at the second mounting location, the first tower having a first track to receive the first pivot pin at a variable position within the first track,
      a second tower for supporting the adjustable transducer hold down fixture, a third base of the second tower being magnetic and positioned to bond to the outer pipe wall at the third mounting location when the third base is positioned substantially tangential to the outer pipe wall at the third mounting location, the second tower having a second track to receive the second pivot pin at a variable position within the first track, and
      two or more fasteners for collectively making rigid the adjustable transducer hold down fixture by restricting adjustment of the first tower about the first pivot pin in the first track and by restricting adjustment of the second tower about the second pivot pin in the second track.

2. A high-precision corrosion monitoring sensor assembly as defined in claim 1, wherein the first base of the ultrasonic transducer is positioned to bond to an outer pipe wall of the pipe using an epoxy bond.

3. A high-precision corrosion monitoring sensor assembly as defined in claim 2, wherein the epoxy bond is an ultrasonic couplant.

4. A high-precision corrosion monitoring sensor assembly as defined in claim 1, wherein each of the first tower and the second tower include a magnet positioned at a respective one of the second base and third base.

5. A high-precision corrosion monitoring sensor assembly as defined in claim 1, wherein the ultrasonic transducer includes a delay line for separating a sensor element of the ultrasonic transducer from the outer pipe wall 160 such that measurements made by the ultrasonic transducer are enhanced.

6. A high-precision corrosion monitoring sensor assembly as defined in claim 1, wherein the first mounting location, the second mounting location, and the third mounting location are points of a common arc of the outer pipe wall, the outer pipe wall having any diameter greater than six (6) inches.

7. A high-precision corrosion monitoring sensor assembly as defined in claim 6, wherein the first track and the second track are positioned on the first tower and the second tower, respectively, so that the second base of the first tower and the third base of the second tower can be positioned substantially tangential to the outer pipe wall.

8. A high-precision corrosion monitoring sensor assembly as defined in claim 6, wherein the first axis and the second axis are orthogonal to a plane containing the common arc.

9. A high-precision corrosion monitoring sensor assembly as defined in claim 1, wherein the first mounting location, the second mounting location, and the third mounting location are coplanar.

10. A high-precision corrosion monitoring sensor assembly as defined in claim 9, wherein the first axis and the second axis are parallel to a plane containing the first mounting location, the second mounting location, and the third mounting location.

11. A high-precision corrosion monitoring sensor assembly as defined in claim 1, wherein the cross-member attaches to one of the ultrasonic transducer or the housing using a threaded mount, the cross-member and one of the ultrasonic transducer or the housing including compatible screw threads.

12. A high-precision corrosion monitoring sensor assembly as defined in claim 1, wherein the cross-member attaches to a housing for the ultrasonic transducer, the housing attaching to the ultrasonic transducer by a clamping force applied by the housing.

13. A high-precision corrosion monitoring sensor assembly as defined in claim 12, wherein the cross-member attaches to the housing for the ultrasonic transducer using one or more slider screws.

14. A high-precision corrosion monitoring sensor assembly as defined in claim 13, wherein one or more slider screws are wrapped by a substantially coaxial coil spring for biasing the housing and the ultrasonic transducer in the direction of the outer pipe wall.

15. A high-precision corrosion monitoring sensor assembly as defined in claim 12, wherein the cross-member attaches to one of the ultrasonic transducer or the housing using a threaded mount, the cross-member and one of the ultrasonic transducer or the housing including compatible screw threads.

16. A high-precision corrosion monitoring sensor system for measuring remaining wall thickness of vessels having any diameter within a preselected range of diameters, the high-precision corrosion monitoring sensor system comprising:
- a plurality of high-precision corrosion monitoring sensor assemblies as defined in claim 1 for measuring remaining wall thickness of a respective vessel segment;
- a pulser in communication with the plurality of high-precision corrosion monitoring sensor assemblies to send and receive signals from the plurality of high-precision corrosion monitoring sensor assemblies;
- an oscilloscope in communication with the pulser to acquire data responsive to received signals; and
- a data analysis system in communication with the oscilloscope to estimate remaining wall thickness of the vessel segment responsive to the data acquired at the oscilloscope.

17. A high-precision corrosion monitoring sensor system as defined in claim 16, wherein the first tower and the second tower of each of the plurality of high-precision corrosion monitoring assemblies are positioned with respect to a respective cross-member responsive to a diameter of a corresponding vessel.

18. A high-precision corrosion monitoring sensor system as defined in claim 17, the high-precision corrosion monitoring sensor system further comprising:
- a plurality of thermometers for measuring the surface temperature of a respective vessel segment corresponding to one of the plurality of high-precision corrosion monitoring sensor assemblies; and
- wherein the data analysis system is configured to estimate wall thickness further responsive to a surface temperature.

19. A high-precision corrosion monitoring sensor system as defined in claim 16, wherein each of the plurality of high-precision corrosion monitoring sensor assemblies are attached to the pulser by a respective coaxial cable of a plurality of coaxial cables, each of the plurality of coaxial cables having a length less than or equal to fifty (50) meters.

20. A high-precision corrosion monitoring sensor system as defined in Claim 16, wherein the data analysis system is configured to determine wall thickness responsive to time differences between adjacent back wall signals.

21. A high-precision corrosion monitoring sensor system as defined in claim 16, wherein the data analysis system is configured to determine wall thickness responsive to the separation of pulse widths of the envelopes of one front wall signal and one back wall signal.

22. A high-precision corrosion monitoring sensor system as defined in claim 16, the high-precision corrosion monitoring sensor system further comprising:
- a plurality of thermometers for measuring the surface temperature of a respective vessel segment corresponding to one of the plurality of high-precision corrosion monitoring sensor assemblies; and
- wherein the data analysis system is configured to estimate wall thickness further responsive to a surface temperature.

\* \* \* \* \*